(12) United States Patent
Sonnenschein et al.

(10) Patent No.: US 7,841,347 B2
(45) Date of Patent: Nov. 30, 2010

(54) METHOD OF PERFORMING SURGICAL PROCEDURES ON PATIENTS SUFFERING FROM HIATAL HERNIA

(75) Inventors: Elazar Sonnenschein, Beer Sheva (IL); Minelu Sonnenschein, Meitar (IL); Avi Roy Shapira, Beer Sheva (IL)

(73) Assignee: Medigus Ltd., Omer (IL)

( * ) Notice: Subject to any disclaimer, the term of this patent is extended or adjusted under 35 U.S.C. 154(b) by 574 days.

(21) Appl. No.: 11/900,182

(22) Filed: Sep. 10, 2007

(65) Prior Publication Data

US 2009/0065003 A1    Mar. 12, 2009

(51) Int. Cl.
*A61B 19/00* (2006.01)
*A61M 16/00* (2006.01)
*A62B 7/00* (2006.01)

(52) U.S. Cl. ............................ 128/898; 128/204.18
(58) Field of Classification Search ............... 128/898, 128/204.18; 227/175, 178, 179, 181, 19, 227/901; 606/139, 142, 143, 148, 151, 152, 606/153

See application file for complete search history.

(56) References Cited

U.S. PATENT DOCUMENTS

| 5,403,326 | A | * | 4/1995 | Harrison et al. ............. 606/139 |
| 7,156,863 | B2 |  | 1/2007 | Sonnenschein et al. |
| 7,735,491 | B2 | * | 6/2010 | Doshi et al. ............ 128/207.18 |
| 2007/0295338 | A1 | * | 12/2007 | Loomas et al. ......... 128/207.18 |
| 2008/0097487 | A1 | * | 4/2008 | Pool et al. ................... 606/151 |

FOREIGN PATENT DOCUMENTS

WO    2007022029    2/2007

* cited by examiner

*Primary Examiner*—David Isabella
*Assistant Examiner*—Andrew Iwamaye
(74) *Attorney, Agent, or Firm*—Roach Brown McCarthy & Gruber, P.C.; Kevin D. McCarthy

(57) ABSTRACT

The invention is a method of lowering the gastroesophageal junction below the diaphragm of a patient with a hiatal hernia during the performance of surgical procedures performed via natural orifices. The method comprises applying positive pressure ventilation with positive end expiratory pressure (PEEP) to the patient.

17 Claims, 37 Drawing Sheets

METHOD OF PERFORMING SURGICAL PROCEDURES ON PATIENTS SUFFERING FROM HIATAL HERNIA

FIELD OF THE INVENTION

The invention is related to the field of surgical procedures which are performed via natural orifices. Specifically the invention relates to the field of endoluminal or natural orifice surgical procedures carried out on the stomach or esophagus.

BACKGROUND OF THE INVENTION

Sliding hiatal hernia (HH) is not a disease but is a normal consequence of aging. The gap between the crura of the diaphragm, through which the esophagus passes, tends to enlarge with age, and up to 70% of the population over the age of 70 has hiatal hernias of this sort. In some patients that suffer from Gastro Esophageal Reflux Disease (GERD), the HH slides into the chest, thus, GERD is considered to be caused by the HH. Therefore, in a surgical procedures (laparoscopically or open fundoplication) for such patients, the HH will also be corrected.

In normal breathing, the air moves into the lungs because the pressure in the chest is negative, consequently, the pressure in the abdominal cavity is higher than the pressure in the chest. When the hiatus is enlarged, the negative pressure inside the chest pulls the stomach up through the gap each time the person takes a breath. When the person exhales, if he/she is lying down, the stomach may stay up; but, if he/she is standing, it is pulled down by gravity and slides back down.

When trying to perform a medical procedure involving the stomach or esophagus, e.g. a fundoplication, surgical treatment of morbid obesity, correction of a hiatal hernia, or removal of part or parts of the stomach, on a patient who is breathing spontaneously, and is lying supine, a NH often causes a problem which must be dealt with by returning the stomach to its correct anatomical position beneath the diaphragm and keeping it there during the course of the procedure and thereafter.

In U.S. Pat. No. 7,156,863 by the same applicant, the description of which, including publications referenced therein, is incorporated herein by reference, is described an endoscopic method of performing a fundoplication for the treatment of gastroesophageal reflux disease (GERD). In this procedure the wall of the fundus of the stomach is pushed up against the esophagus and is attached to it. The preferred place to attach the tissue of the fundus to that of the esophagus is about 3-5 cm above the junction between the esophagus and the stomach, i.e. the gastroesophageal junction or Z-line. In the case of a patient with HH, this might not be possible unless some way is found to keep the stomach from being pulled up through the hiatus as the patient breathes.

Many different ways for accomplishing this by grabbing the tissue of the stomach or esophagus or both and pulling the grabbed tissue to the desired position are known in the art. For example WO 2007/022029 describes a device used to create a gastroesophageal flap restoration. The device has a plurality of orifices distributed about the outer surface of a part of the longitudinal insertion member when the insertion member is inserted into the esophagus to the desired depth relative to the Z-line, vacuum is applied through the orifices to hold the inner wall of the esophagus to the outside of the insertion member. The insertion member is then pushed downward to correct the hernia and the procedure is then carried out.

It is a purpose of the present invention to provide a simple, safe method of preventing the junction of the stomach and the esophagus to slide into the chest in patients with HH during the performance of surgical procedures carried out on the stomach or esophagus.

Further purposes and advantages of this invention will appear as the description proceeds.

SUMMARY OF THE INVENTION

The invention is a method of lowering the gastroesophageal junction below the diaphragm of a patient with a sliding hiatal hernia during the performance of surgical procedures performed via natural orifices. The method comprises applying positive pressure ventilation with positive end expiratory pressure (PEEP) to the patient. The method may also comprise tilting the operating table slightly downwards. In an embodiment a PEEP of 5-10 mmHg is applied during the entire course of the procedure.

A large variety of medical procedures can be performed using the method of the invention. For example, after the PEEP has been applied to lower the gastroesophageal junction below the diaphragm, the stomach can be joined to the esophagus by applying fixing means, e.g. clips, sutures, staples, glue; a fundoplication can be performed; the stomach and/or the esophagus can be joined to other organs; a procedure for surgical treatment of morbid obesity may be carried out; a hiatal hernia can be corrected; part or parts of the stomach can be removed; one or more implanted devices can be inserted or attached to the esophagus or the stomach wall; one or more external devices can be attached to the stomach wall; the stomach can be divided by use of an external stapler or an endoscopic stapler or endoscopic suturing machine; and the intestine can be treated or part of it removed.

A large variety of transgastric medical procedures can be performed using the method of the invention. For example, after the PEEP has been applied to lower the gastroesophageal junction below the diaphragm, an incision is made in the stomach and then: the stomach can be transgastrically joined to the small intestine by applying fixing means, the stomach can be transgastrically, transvaginally, or transrectally divided into two different volumes, a transgastric, transvaginal, or transrectal fundoplication comprising joining the stomach to the esophagus by applying fixing means can be performed.

All the above and other characteristics and advantages of the invention will be further understood through the following illustrative and non-limitative description of embodiments thereof, with reference to the appended drawings. In the drawings the same numerals are sometimes used to indicate the same elements in different drawings.

DETAILED DESCRIPTION OF PREFERRED EMBODIMENTS

The method of the invention is dependent on performing the procedure under general anesthesia. During general anesthesia the patient does not breathe naturally but gets positive pressure ventilation. The air is not sucked into the lungs as in natural breathing, but is pushed into the lungs by the bellows in the ventilator. As a consequence the pressure inside the chest is higher than the pressure in the abdomen and the stomach is pushed down into the abdomen where the surgeon wants it.

In normal breathing, the pressure is an inverted sinusoidal wave which goes from 0 to minus 5 or 10 mmHg and back to 0. In positive pressure ventilation exhalation is passive. The pressure goes from 0 to about plus 20 mm Hg (even higher, if the lung compliance is poor) and back to 0. For a patient with normal lungs, the pressure stays at 0 for about $\tfrac{2}{5}^{th}$ of the cycle. During this rest period, known as the expiratory plateau, the location of the GastroEsophageal (GE) junction in the supine patient is not reliable, particularly when insufflation of air into the stomach increases the abdominal pressure.

Positive End Expiratory Pressure (PEEP) is a technique used with artificial ventilation to maintain a positive pressure in the airway at the end of the passive exhalation.

The method of the invention calls for the application of a PEEP of approximately 5-10 mmHg during the part of or the entire course of the procedure. This, optionally combined with tilting the operating table slightly downwards, will pull the Z-line below the diaphragm and ensure that the stomach will remain in the abdomen even when the hiatal gap is large. It is to be noted that higher values of PEEP will also have the same effect, but are not necessary, and may lead to complications.

Figure 2:
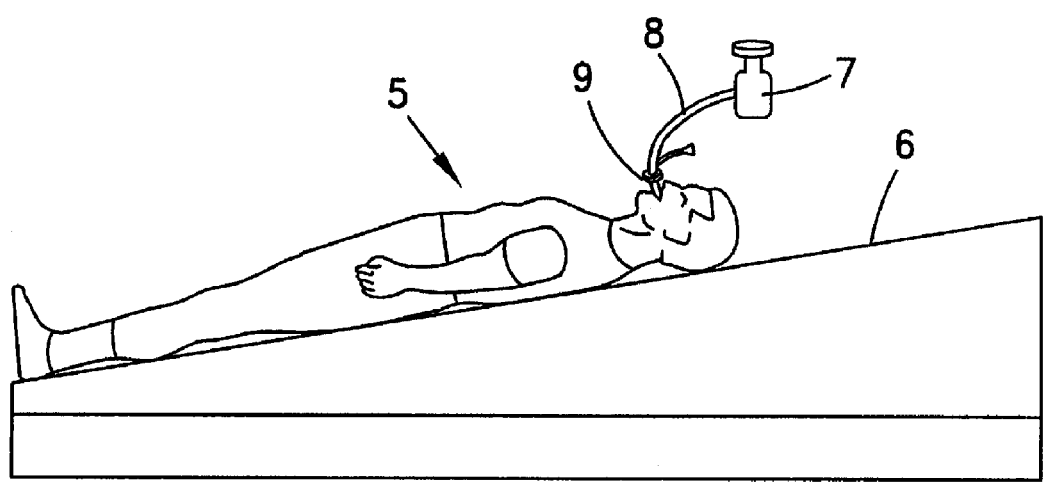
FIG. 2 schematically shows the main features of the operating room arrangement.

The main features of the operating room arrangement that are needed to illustrate the invention are shown schematically in FIG. 2. Patient 5 is lying on his back on table 6, which is arranged to be tilted slightly downwards (note that the tilt angle is exaggerated in the figure). PEEP is applied to patient 5 by supplying air at 5-10 mmHg from air supply 7 through tube 8 that is connected to endotracheal tube.

Figure 1A:
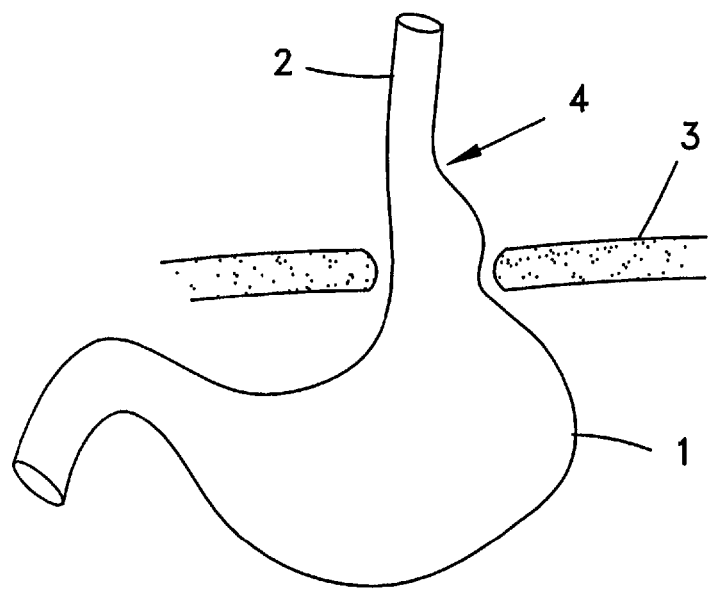
FIG. 1A schematically shows the position of the gastroesophageal junction (GEJ) relative to the diaphragm in a patient that suffers from a sliding hiatal hernia.
Figure 1B:
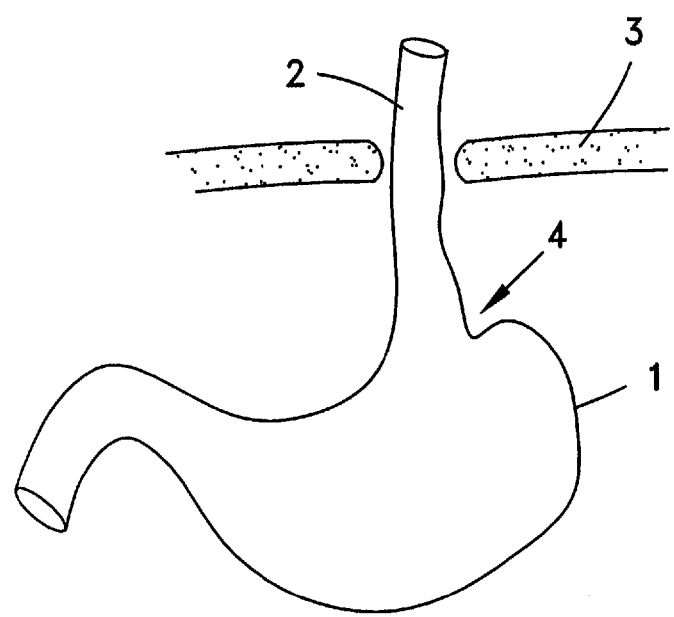
FIG. 1B schematically shows the position of the gastroesophageal junction (GEJ) relative to the diaphragm in a patient after applying positive end expiratory pressure (PEEP) to the patient according to the method of the invention.

FIG. 1A schematically shows the position of the gastroesophageal junction (GEJ) 4 relative to the diaphragm 3 in a patient that suffers from a sliding hiatal hernia. FIG. 1B schematically shows the position of the gastroesophageal junction (GEJ) relative to the diaphragm in a patient after applying positive end expiratory pressure according to the method of the invention. In the figures are also shown the patient's stomach 1 and esophagus 2.

Once the HH has been reduced using PEEP as described herein, it is possible to safely carry out medical procedures involving the stomach or esophagus. A non-exclusive list of such procedures includes: joining the stomach to the esophagus by applying piercing, and/or fixing means, e.g. clips, staples, glue, or sutures; different fundoplication procedures (direct endoscopic, transgastric, transvaginal and transrectal); surgical treatments or procedures of morbid obesity; correction of only the hiatal hernia; removal of part or parts of the stomach; inserting or attaching one or more implanted devices to the esophagus or the stomach; inserting or attaching one or more external mechanical and/or electronic devices to the stomach; dividing the stomach by use of an external stapler or an endoscopic stapler; treatment or removal of part of the intestine and attaching the stomach to the small intestine by applying fixing and/or join means.

Recently transgastric procedures have been proposed by the applicant of the present application and others. For example, U.S. patent application Ser. Nos. 11/446,740 and 11/825,694 by the same applicant, the descriptions of which, including publications referenced therein, are incorporated herein by reference respectively describe a transgastric method for carrying out a partial fundoplication and devices and methods for treating morbid obesity. The method of the present invention to lower the gastroesophageal junction to its natural location below the diaphragm of the patient with a sliding hiatal hernia and to prevent the abdominal esophagus and the stomach or part thereof to slide into the chest can be readily applied during the performance of transgastric, transvaginal or transrectal procedures. A non-exclusive list of such procedures includes: transgastrically joining the stomach to the small intestine by applying fixing or approximation means; transgastrically, transvaginally, or transrectally dividing the stomach into two different volumes; transgastric treatment or removal of part of the intestine, and transgastric, transvaginal, or transrectal fundoplications comprising joining the stomach to the esophagus by applying fixing (join) means, e.g. clips, staples, or sutures.

It should be noted that patients with longstanding large hiatal hernias may have adhesions that may prevent the stomach from sliding down even when the pressure in the chest is positive relative to the abdominal pressure. Therefore, although the method of the invention is applicable for most patients with small (up to 3 or maybe even 4 cm) hiatal hernias, it may not be applicable to all. The patients in whom the hernia will not slide back can easily be identified by taking an upright chest X-ray before the procedure.

FIGS. 3A, 3B, 3C, and 3D schematically show steps of a fundoplication procedure carried out on a patient suffering from sliding hiatal hernia according to the method of the invention. When laid on the operating table the GEJ of the patient slides above his diaphragm as shown in FIG. 1A. PEEP is then applied as shown in FIG. 2. With the PEEP applied continuously during the entire procedure, the GEJ of the patient below the diaphragm as shown in FIG. 1B and the fundoplication procedure can be carried out.

Figure 3A:
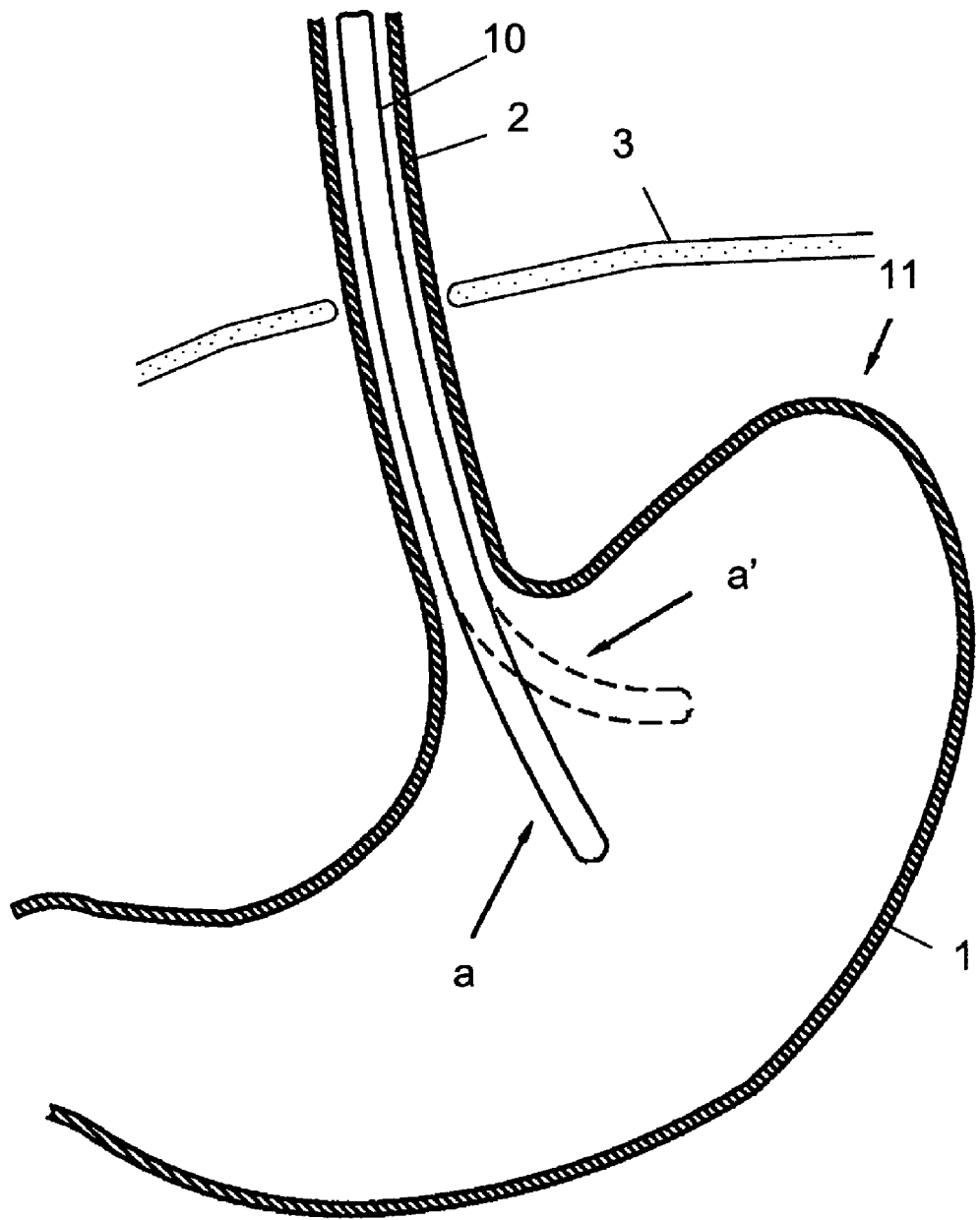
FIGS. 3A, 3B, and 3C schematically show steps of a fundoplication procedure carried out after the GEJ of the patient has been lowered below the diaphragm by applying PEEP according to the method of the invention.

An endoscopic device 10 comprising fixing means, e.g. a stapler, is passed through the mouth and esophagus 2 of the patient into his stomach 1. In FIG. 3A, two positions of the device are shown, a and a'. Position a is the initial position after the device 10 has been inserted the whole of its desired length into stomach 1. Position a' illustrates the beginning of bending of articulation section of the device, towards the fundus 11 of stomach 1.

Figure 3B:
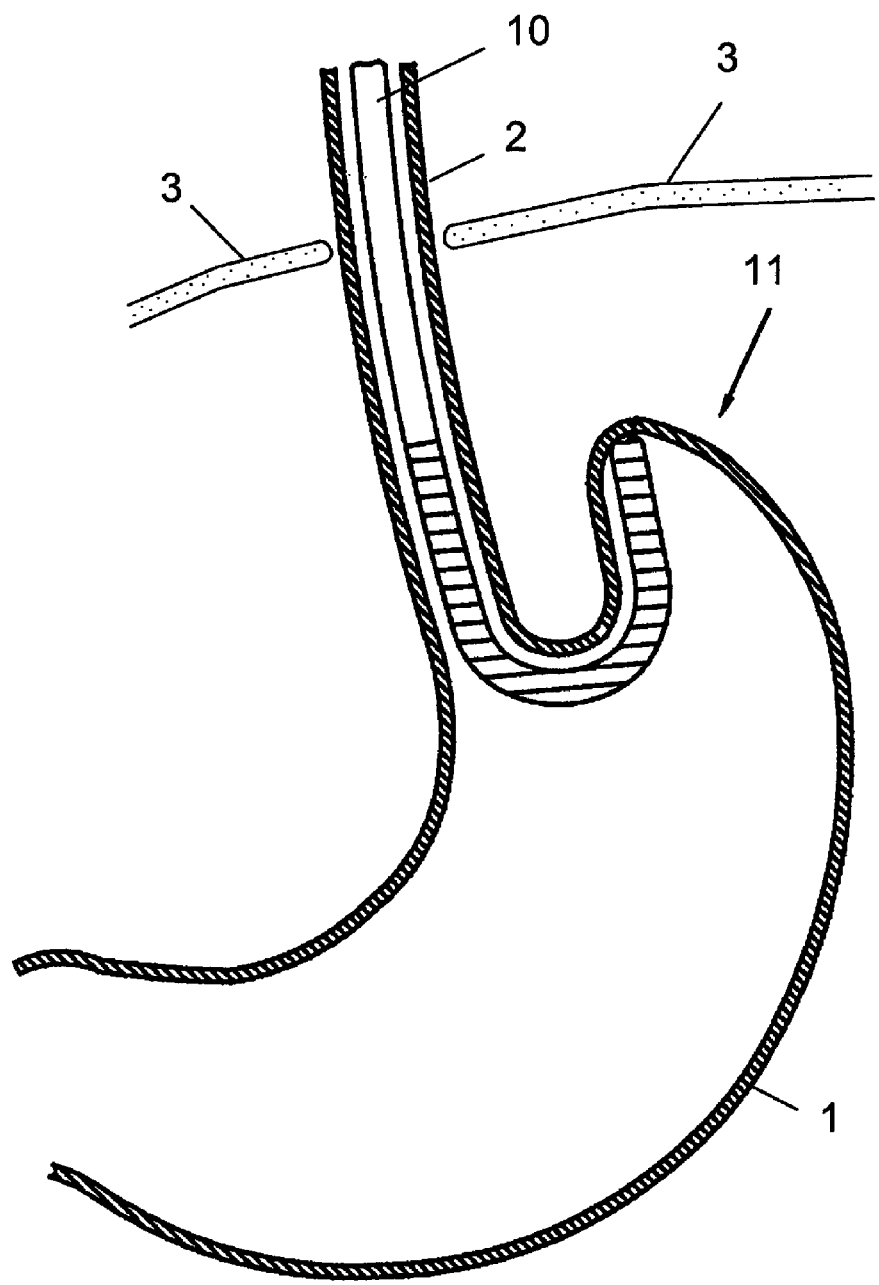

In FIG. 3B, the articulation section of endoscopic device 10 has been bent until the distal tip of the device has encountered the wall of the fundus 11 and has started to push it towards the lower region of the esophagus 2.

Figure 3C:
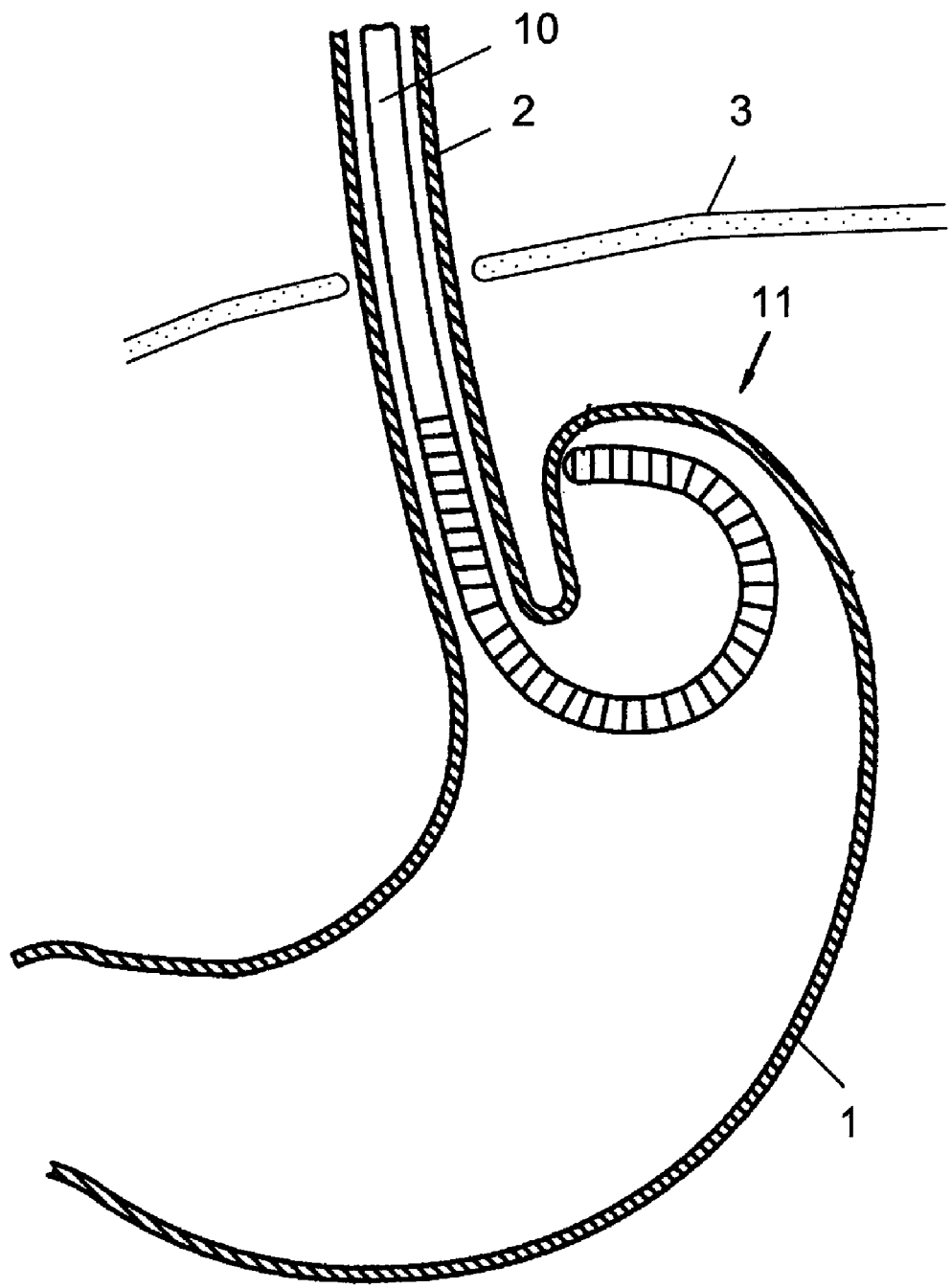

In FIG. 3C, continued bending of the articulation section of device 10 has pushed the fundus 11 from its original position to a position near the lower esophagus 2. In this position, the fundus 11 is correctly positioned by the tip of endoscopic device 10 and it is possible to carry out the stapling together of the fundus 11 and esophagus 2.

Figure 3D:
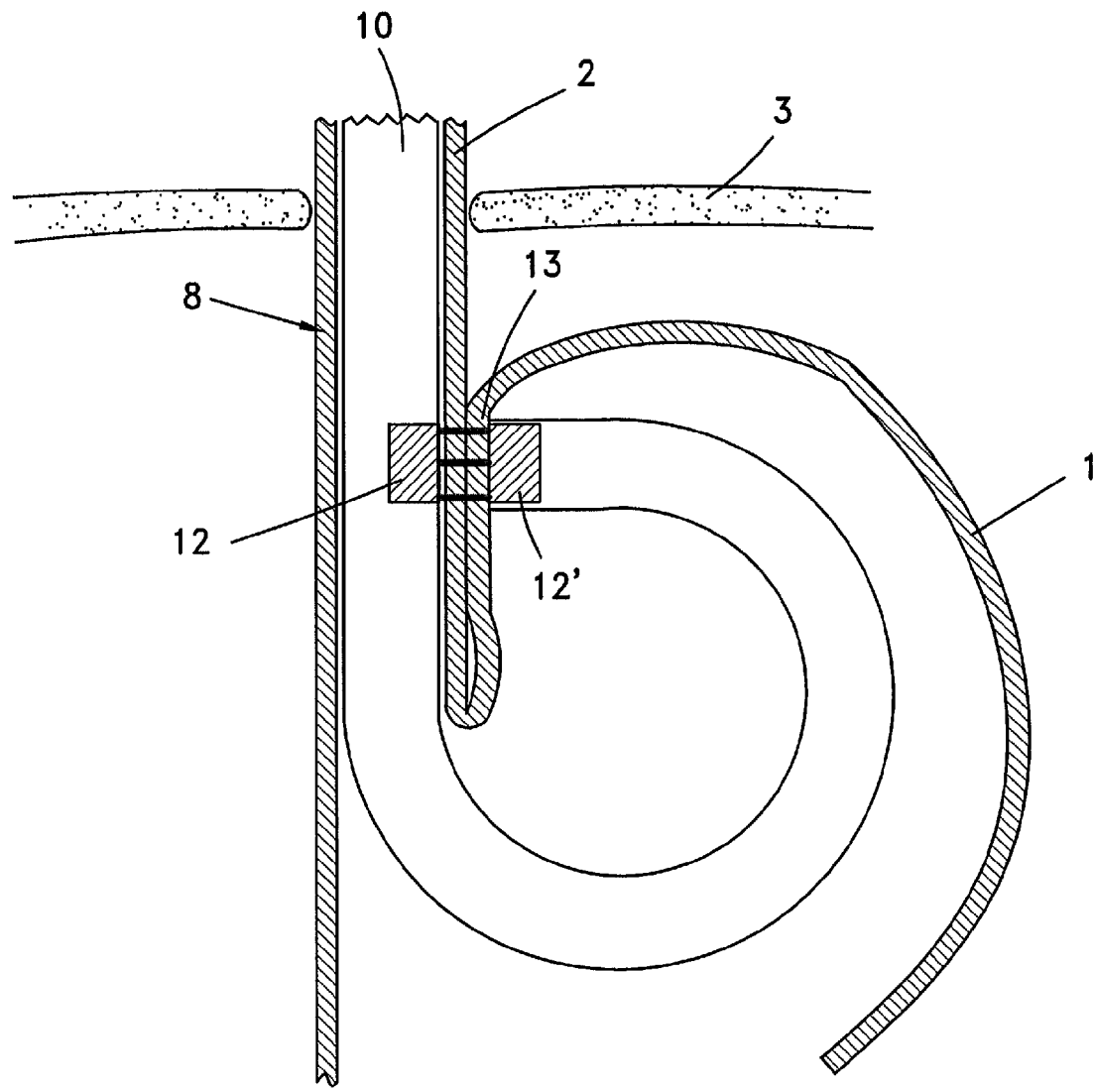
FIG. 3D schematically shows the final step of the fundoplication procedure after staples have been fired to join the patient's stomach to his/her esophagus.

FIG. 3D is a more detailed view of the situation after the articulation of the endoscopic device 10 has been completed. In this figure is schematically shown the final step of the fundoplication procedure after staples 13 have been fired from the staple cartridge portion 12 against the anvil portion 12' of the stapler unit to join the patient's stomach 1 to his/her esophagus 2.

FIGS. 4A to 4D schematically show steps of a transgastric method of applying a gastric band carried out on a patient suffering from morbid obesity and sliding hiatal hernia according to the method of the invention. When laid on the operating table the GEJ of the patient slides above his diaphragm as shown in FIG. 1A. PEEP is then applied as shown in FIG. 2. With the PEEP applied continuously during the entire procedure, the GEJ of the patient below the diaphragm as shown in FIG. 1B and the method of applying a gastric band can be carried out.

Figure 4A:
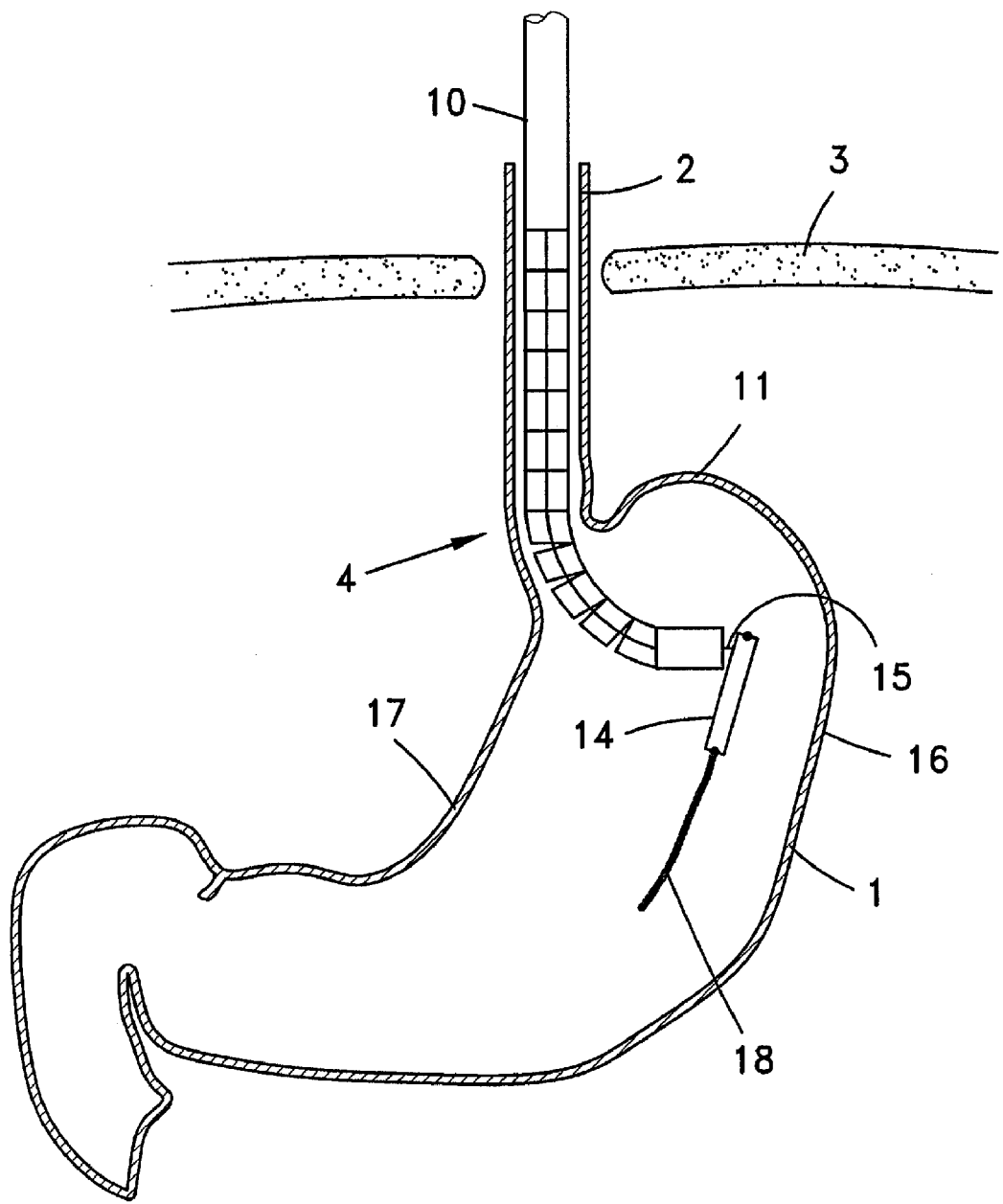
FIGS. 4A to 4D schematically illustrate a transgastric method of applying a gastric band for treating morbid obesity.
Figure 4B:
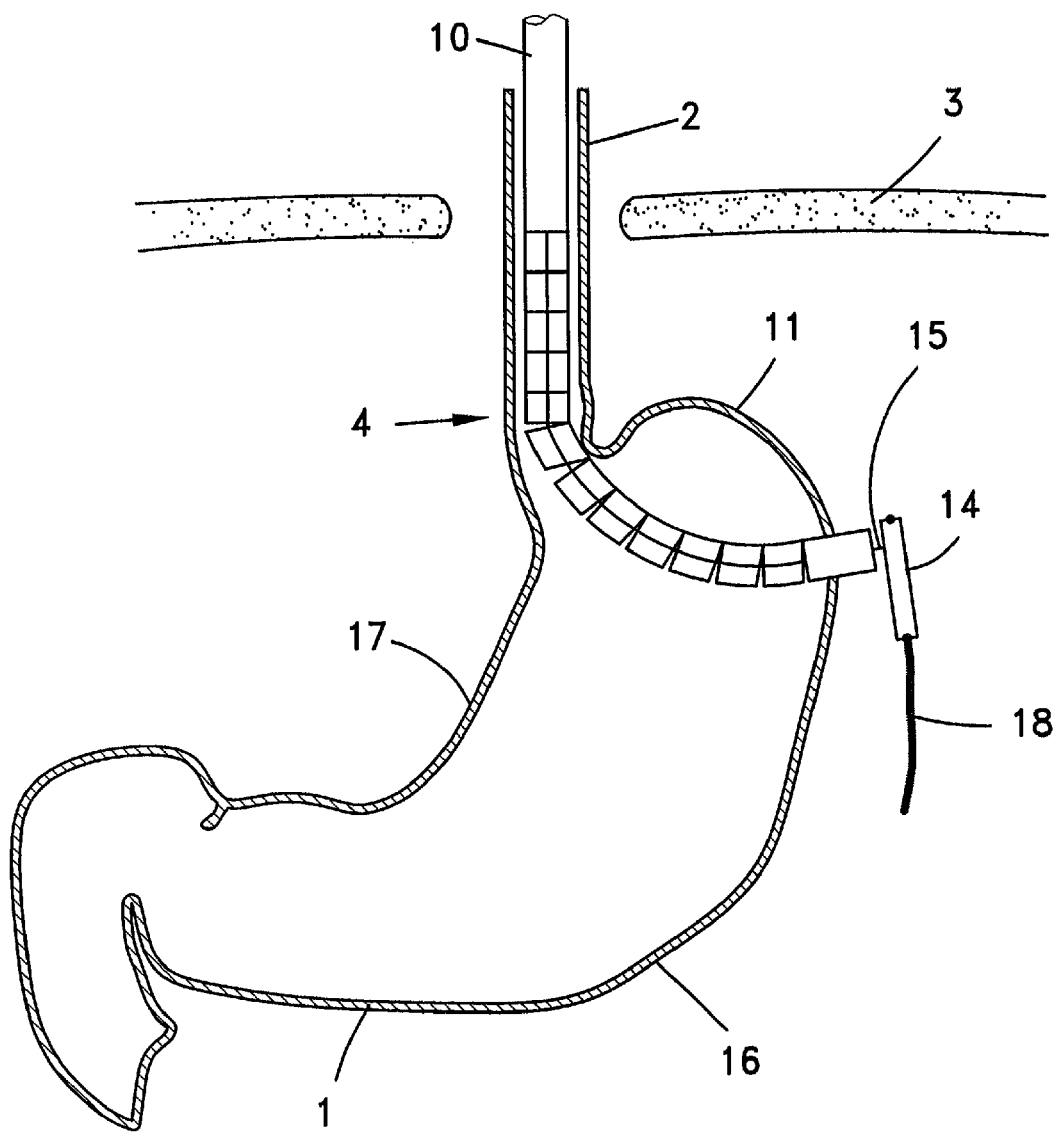
Figure 4C:
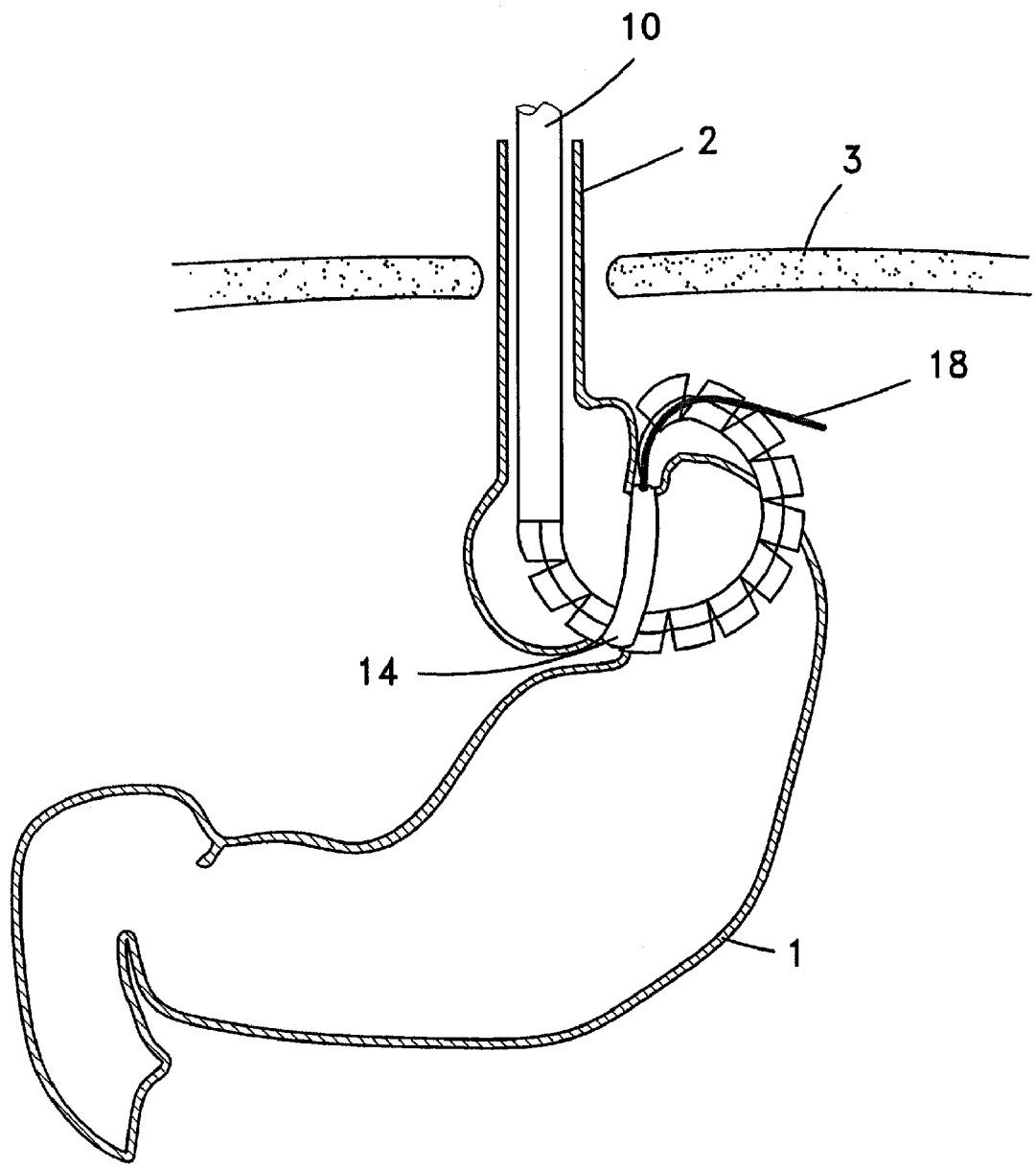
Figure 4D:
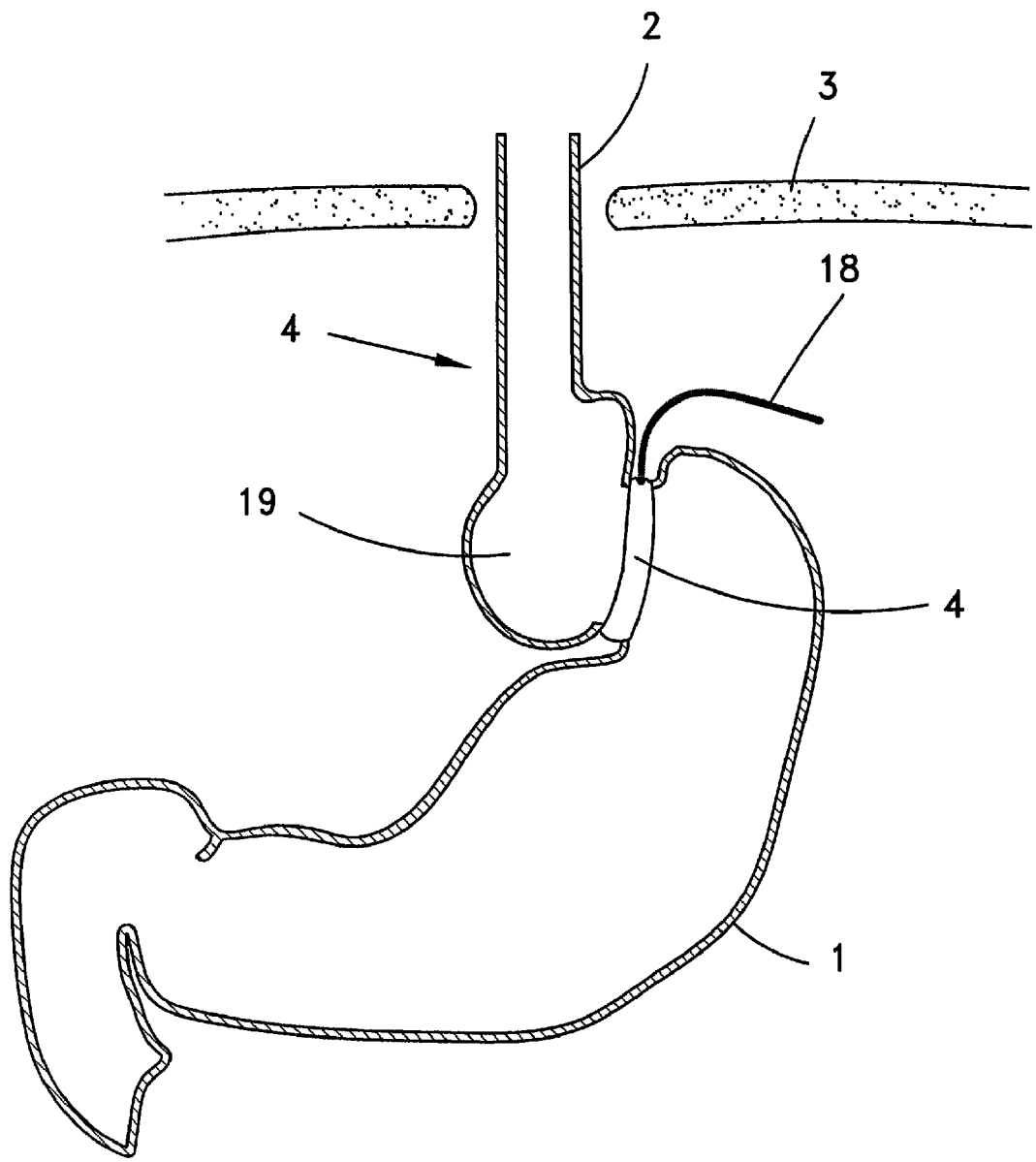

An adjustable band 14 is grasped in front of the distal tip of an endoscope by a forceps 15 that passes through one of the working channels of endoscopic device 10. The adjustable band 12 and endoscope 10 are introduced transorally through the esophagus 2 and the GEJ 4 into the stomach 1 of the patient. Once in the stomach 1 the articulation section of endoscope 1 is bent to bring the distal tip close to the upper part of the greater curve 16 of the stomach 1. At this location a hole is made in the stomach wall by means of a surgical cutting tool that has been introduced to the operating site through a second working channel. The distal end of endoscope 10 and attached band 14 are pushed through the hole (FIG. 4B) and the articulation section bent to bring the distal tip near the fundus 11. Various grasper and separator tools are used to slide the band 14 around the upper part of stomach 1. The band 14 is placed at a diagonal from a location on the fundus 11 slightly above the top of the greater curve 16 to a point on the upper part of the lesser curve 17. Grasping and other tools introduced through the working channels are used to manipulate perigastric tissues, e.g. the fat pad, move the band 14 into position, pull the band tight, and attach its two ends together (FIG. 4C). A baby scope may be introduced through a working channel of endoscope 10 and used to manipulate the band around the posterior side of the stomach under visualization by the distal tip camera of the baby scope. After band 14 is fastened it is released, the articulation section is straightened and repositioned, and the free end of an inflation tube 18 of the band 100 is grasped by a grasping tool and is maneuvered into position and attached to a connection on a port that has been implanted in the abdominal wall of the patient. Finally, the endoscope 10 is withdrawn from the patient. A second endoscope with a front closing stapler mounted on its distal tip is now inserted into the stomach and used to close the hole around the tube 18, after which the stapler is also withdrawn. The result of the procedure is shown in FIG. 4D. Band 14 is wrapped tightly around the stomach 1 forming a small pouch 19 below GEJ 4. Food can flow from pouch 19 into the lower part of the stomach 1 by passing through a stoma created by the band 14. The diameter of the stoma can be adjusted by inserting or withdrawing a fluid such as air or saline solution from a balloon-like compartment on the inside surface of band 14 via the implanted port and tubing 18.

FIGS. 5A to 5G schematically show steps of another method of applying a gastric band carried out on a patient suffering from morbid obesity and sliding hiatal hernia according to the method of the invention. When laid on the operating table the GEJ of the patient slides above his diaphragm as shown in FIG. 1A. PEEP is then applied as shown in FIG. 2. With the PEEP applied continuously during the entire procedure, the GEJ of the patient below the diaphragm as shown in FIG. 1B and the method of applying a gastric band can be carried out.

Figure 5A:
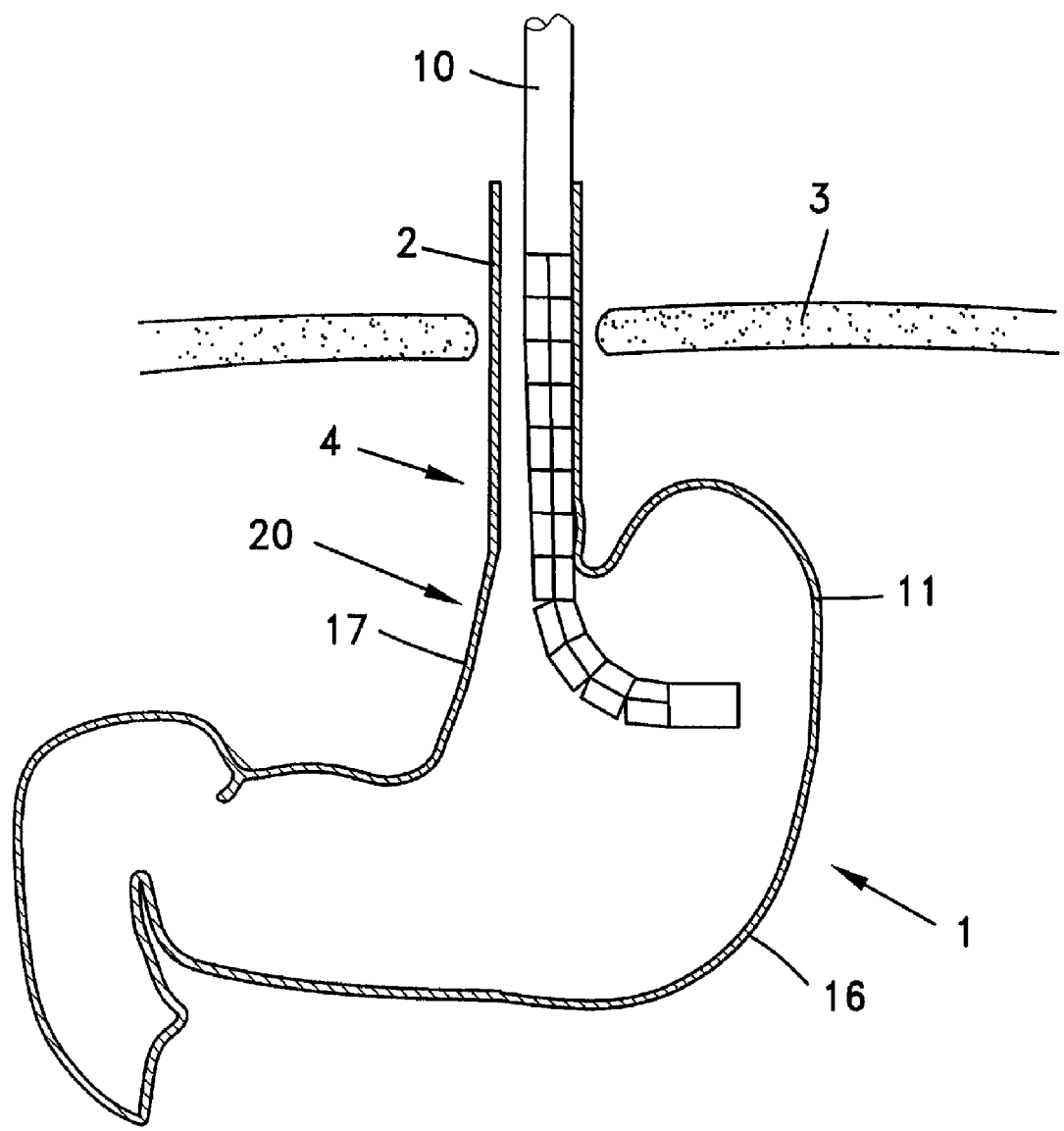
FIGS. 5A to 5G schematically show the steps of another method of inserting a gastric band for treating morbid obesity.
Figure 5B:
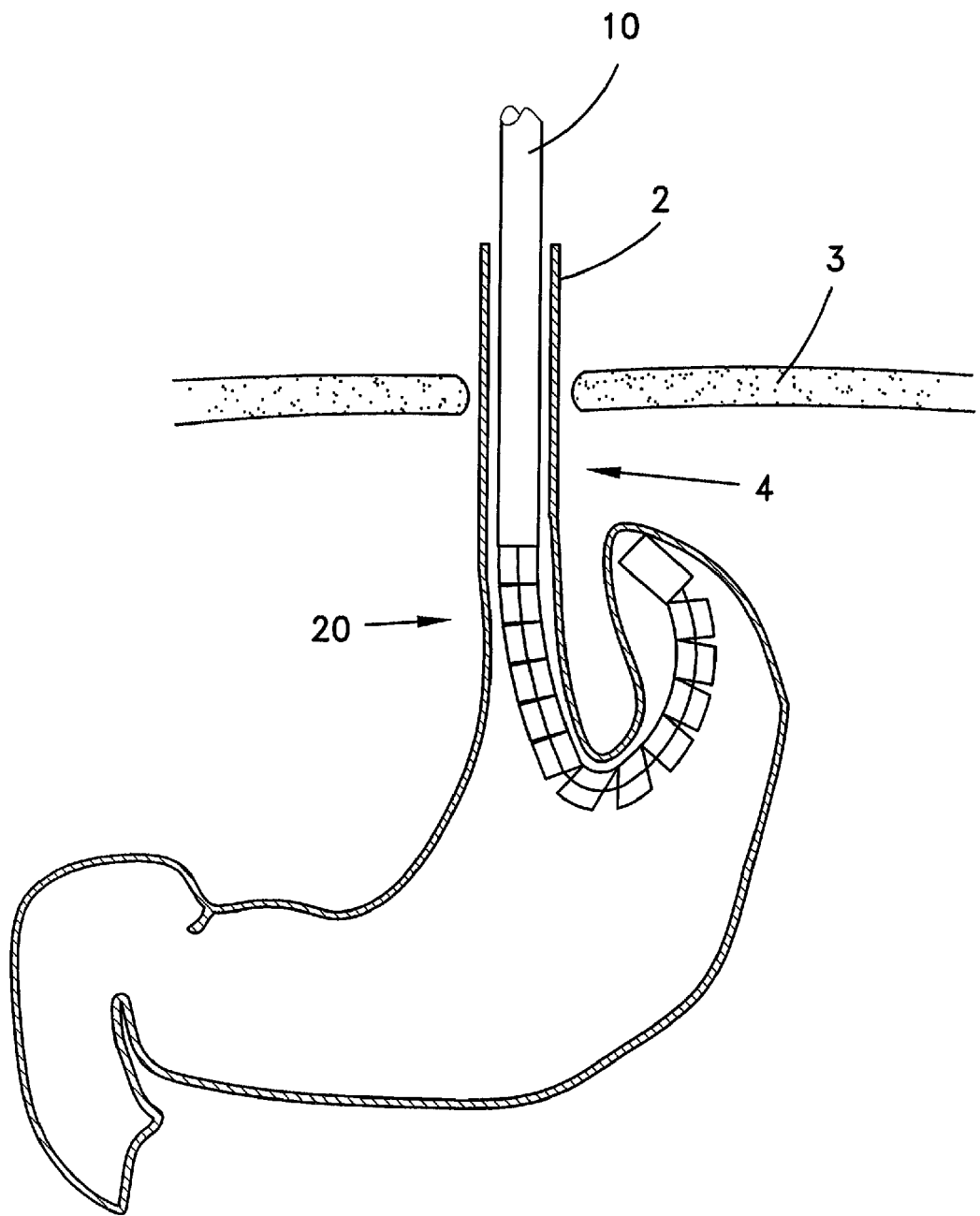
Figure 5C:
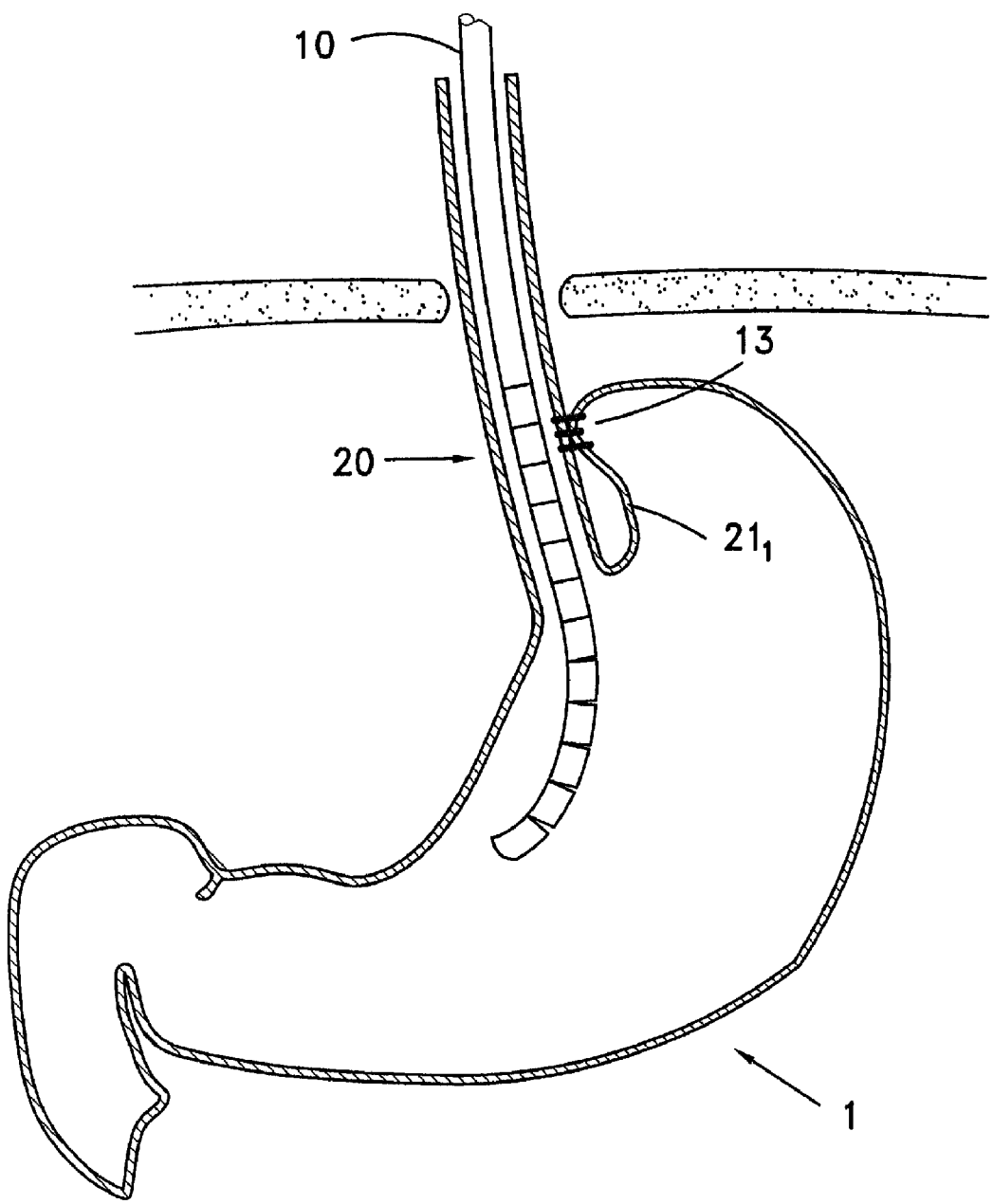
Figure 5D:
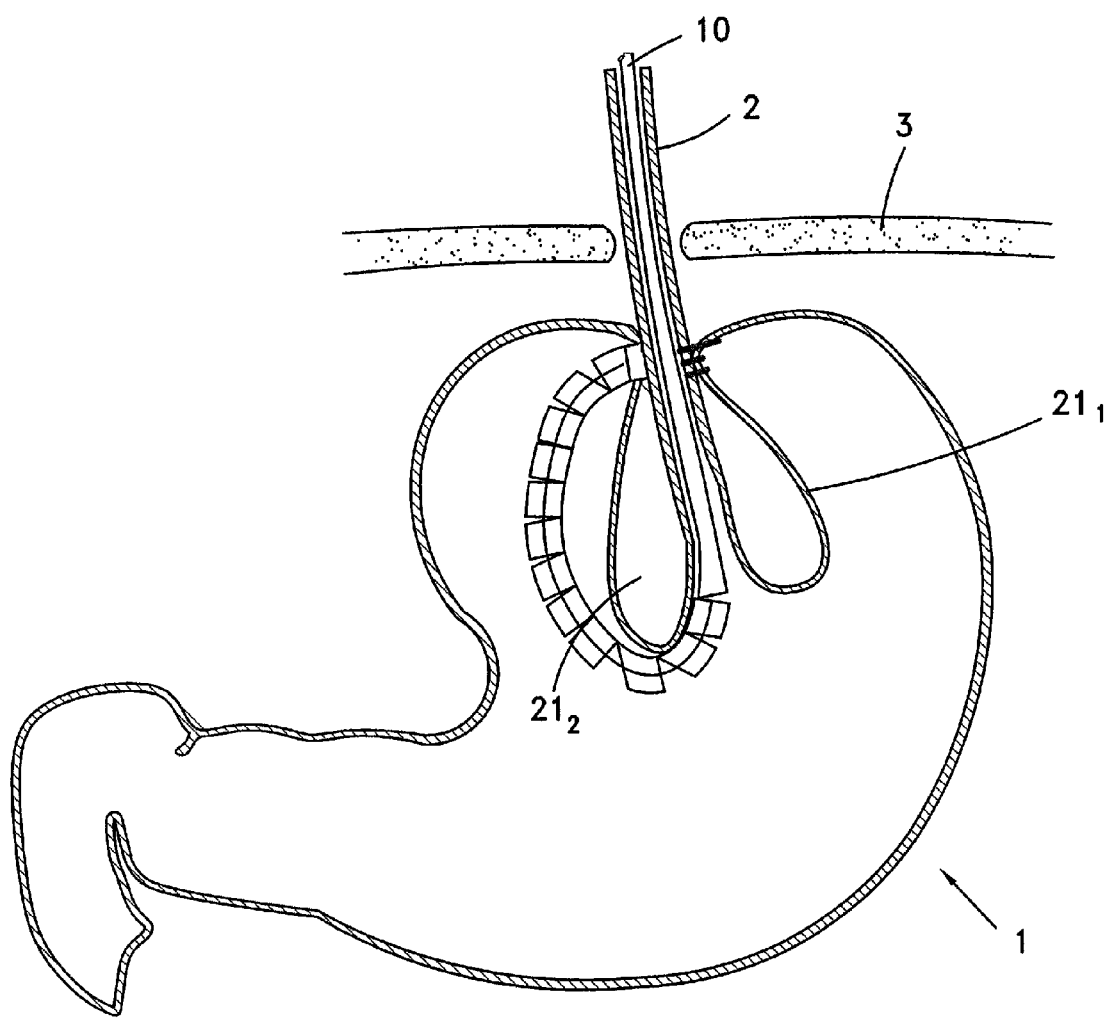
Figure 5E:
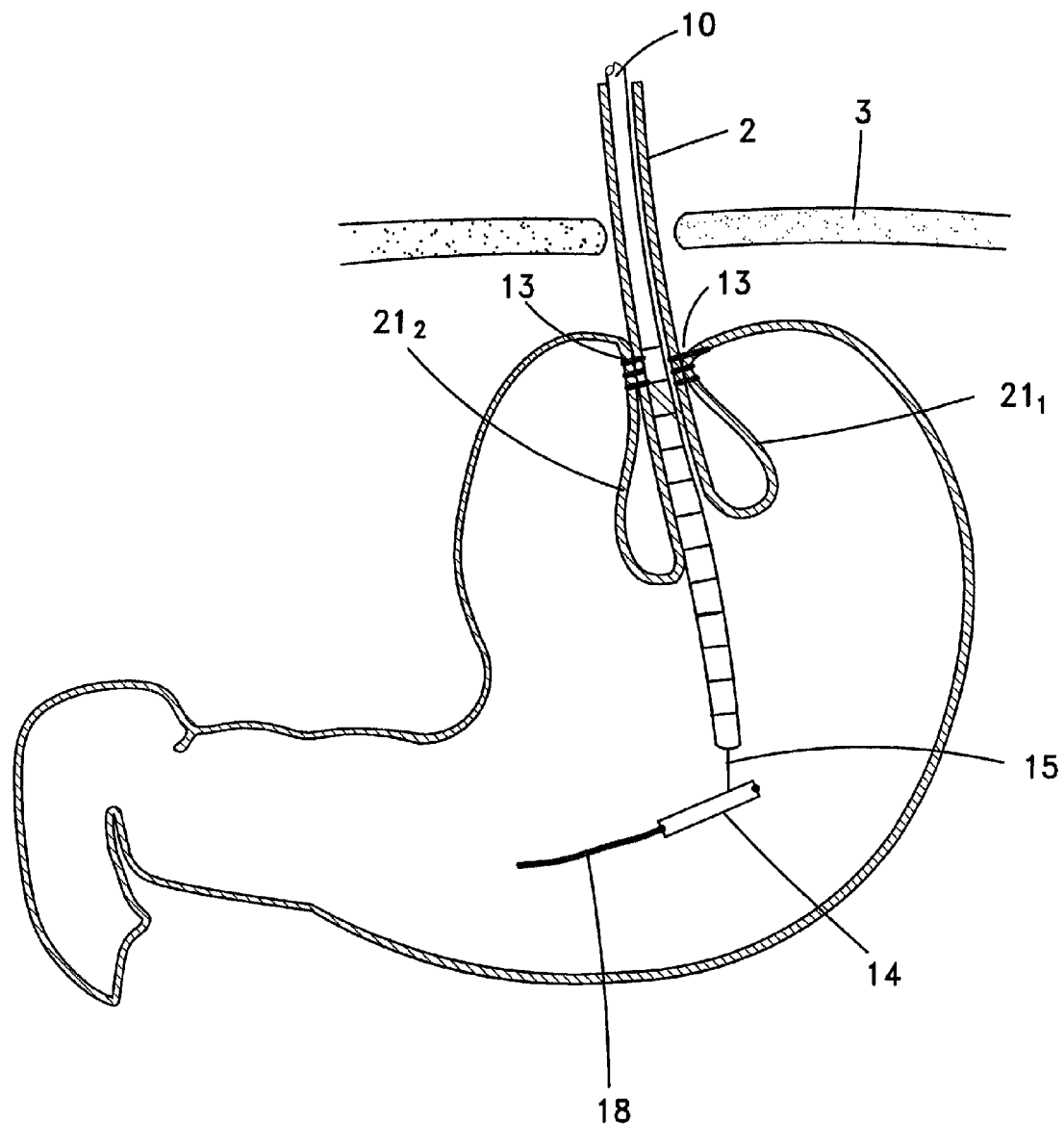
Figure 5F:
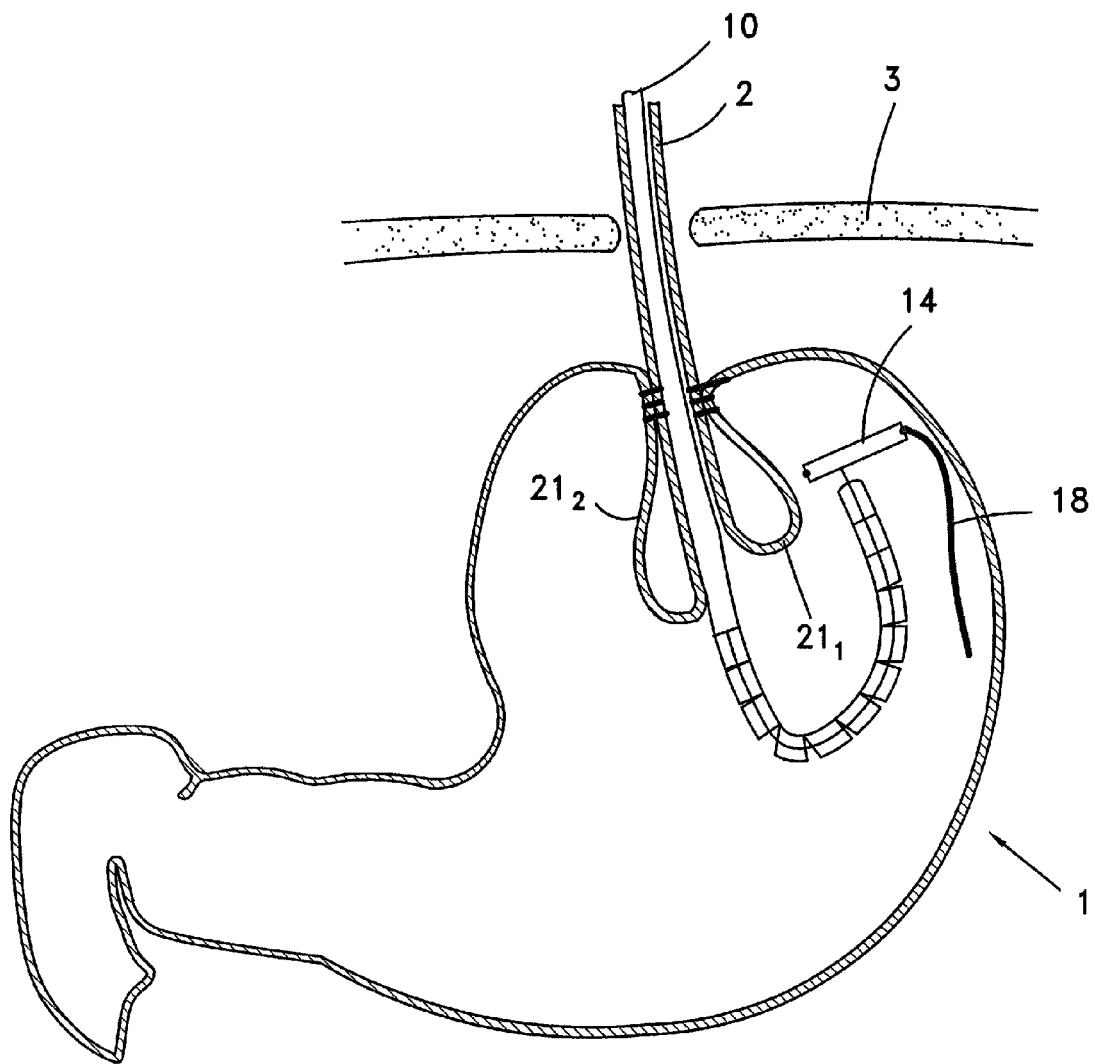

An endoscope 10 is first introduced through the esophagus 2 into the stomach 1 and bent so that the distal tip of the endoscope engages the wall of stomach 1 about at the location where the upper part of the greater curve 16 joins the fundus 202 (FIG. 5A) The articulation section of endoscope 10 is bent further until the outer side of the stomach wall is folded back and pressed against the outer side of the cardia 20 (FIG. 5B). An array of staples 13 is fired to attach the walls to each other creating a full loop $21_1$ (FIG. 5C). The endoscope 10 is then straightened, rotated about 180 degrees and bent and advanced until it contacts the stomach wall along the lesser curvature 17 (FIG. 5C). As before on the other side of the stomach, the stomach wall is raised and the outer wall of the lesser curve is stapled to the wall of the cardia 20 creating full loop $21_2$ (FIG. 5D). This procedure can be repeated to create more than two similar loops if required. The endoscope is now withdrawn from the patient and another endoscopic instrument 10 with an adjustable band 14 held in front of it by a grasping tool 15 is introduced through the esophagus 2 into the stomach 1 (FIG. 5E). The articulation section of the endoscope is bent to bring the distal tip and the band close to the upper part of the stomach (FIG. 5F). Using grasping tools the band is wrapped around the outside of loops $21_1$ and $21_2$ and the ends of the band are joined. Sutures or staples may be put around the band or gastro-gastric sutures applied, as is commonly done, in order to prevent migration or slippage.

Figure 5G:
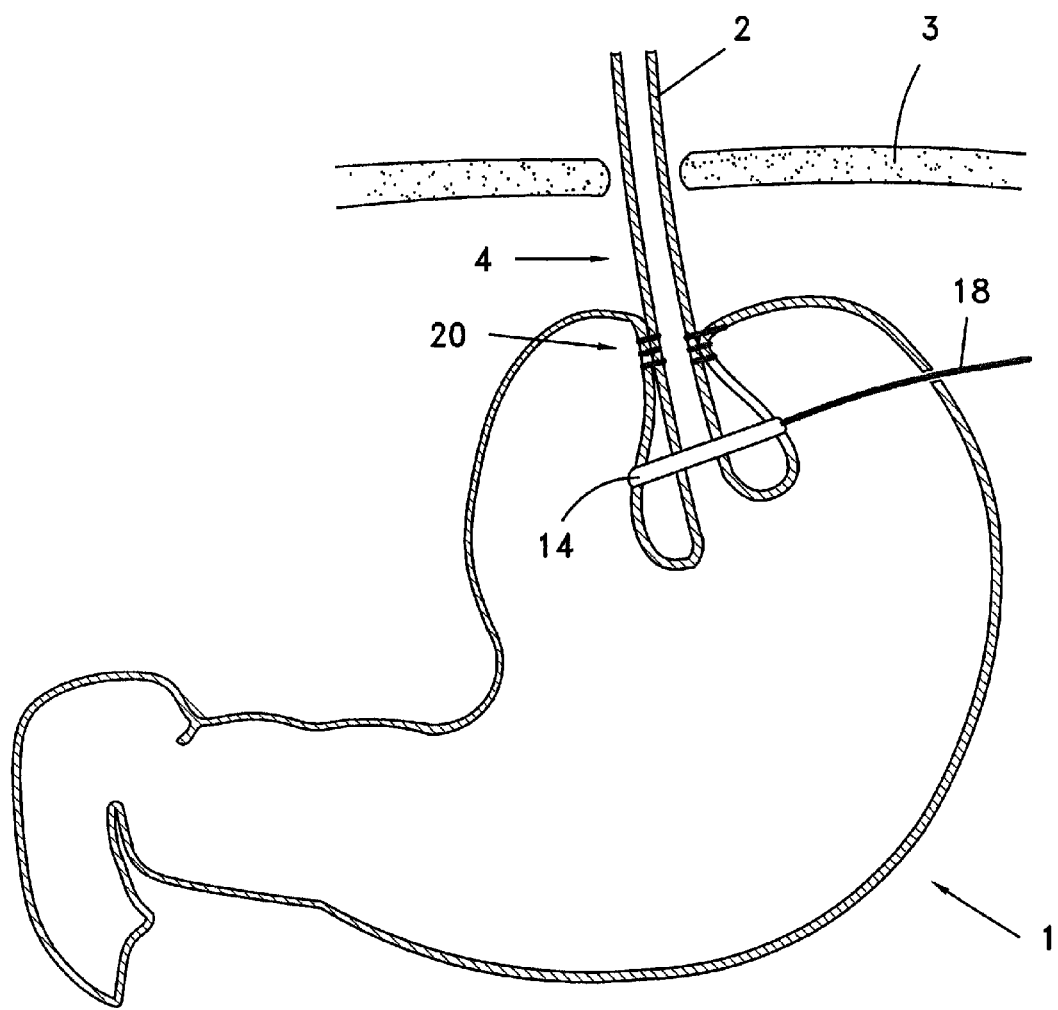

The distal tip of the endoscope 10 is now positioned at the wall of the stomach. A cutting tool is introduced through one of the working channels and a hole made in the stomach wall. The endoscope is pushed through the hole and the free end of the inflation tube 18 of the band 14 is grasped by a grasping tool and is maneuvered into position and attached to a connection on a port that has been implanted in the abdominal wall of the patient. The endoscope is withdrawn from the patient and a third endoscope with a front closing stapler mounted on its distal tip is now inserted into the stomach and used to close the hole around the tube 18, after which the stapler is also withdrawn. The result of the procedure is shown in FIG. 5G.

Figure 6:
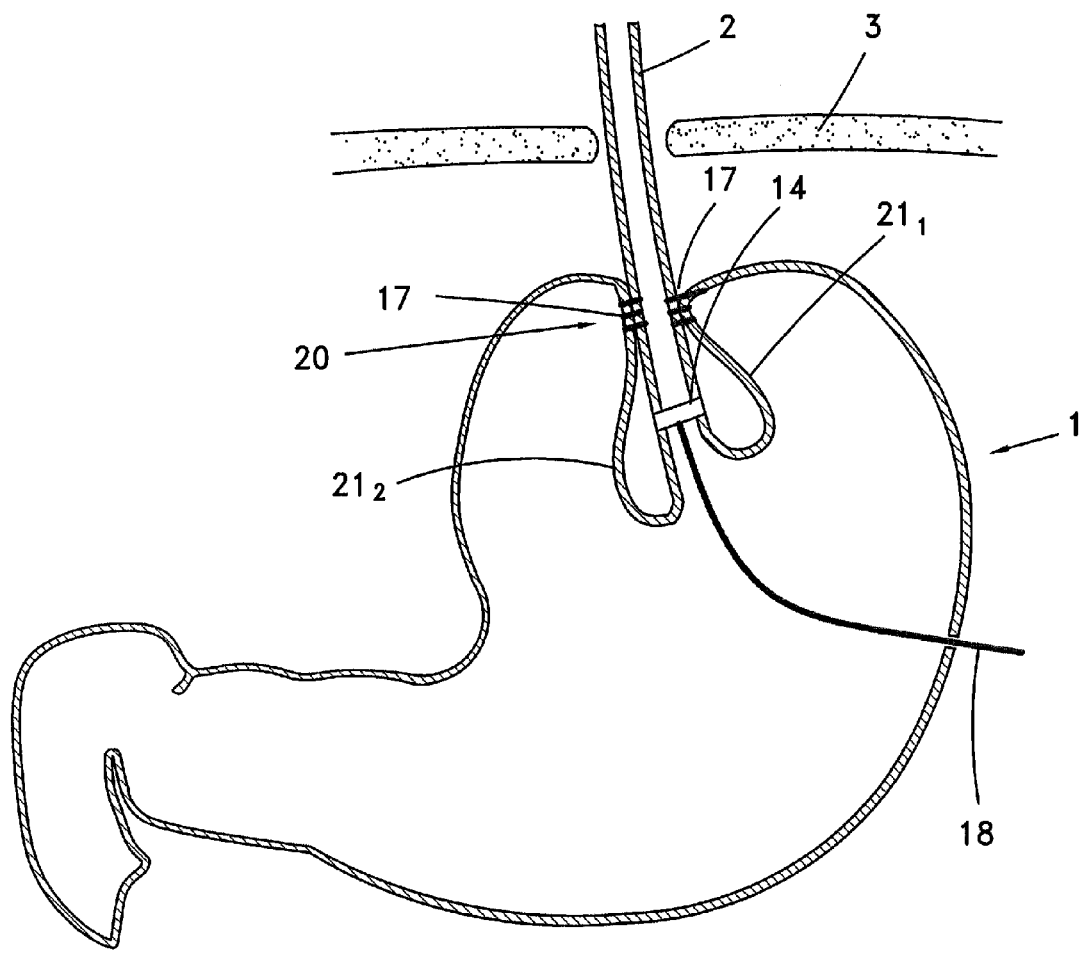
FIG. 6 schematically illustrates the last steps of a third method of inserting a gastric band.

Most of the steps of a third method of inserting a gastric band are essentially the same as those of the previous method. The steps that are shown in FIG. 1A, FIG. 1B, FIG. 2, and FIG. 5A to FIG. 5F are identical. FIG. 6 is used to illustrate the final steps of the procedure. Referring now to FIG. 5F, when the articulation section of the endoscope 10 is bent to bring the distal tip and the band 14 close to the wall of the cardia 20 a cutting tool is passed through a working channel and is used to make a small hole in the lower part of the wall of the cardia 20. Grasping tools passed through the working channel of the endoscope are now used to pull the band 14 out of the stomach 1 through the hole and to wrap it around the outside of the cardia 14 and join the ends of the band together. After the ends of the band are joined, the distal tip of the endoscope is now positioned at the wall of the stomach. A cutting tool is introduced through one of the working channels and a hole made in the stomach wall. The endoscope is pushed through the hole and the free end of the inflation tube 18 of the band 14 is grasped by a grasping tool and is maneuvered into position and attached to a connection on a port that has been implanted in the abdominal wall of the patient (FIG. 6). In this embodiment, the band is held in place around the outer wall of the cardia by the plicated and stapled walls of the stomach. It should be noted that this embodiment can be carried out by stapling the wall of the stomach to the cardia at more than two locations. In addition, it is easier to make the hole and attach the band after the stomach wall is attached on one side only (e.g. as shown in FIG. 5C). If this is done it will be much easier to attach and fasten the band. Also if the second side is stapled after the band is already in place, it can be attached to the cardia such that the band is more tightly held then in the method described above.

Figure 7A:
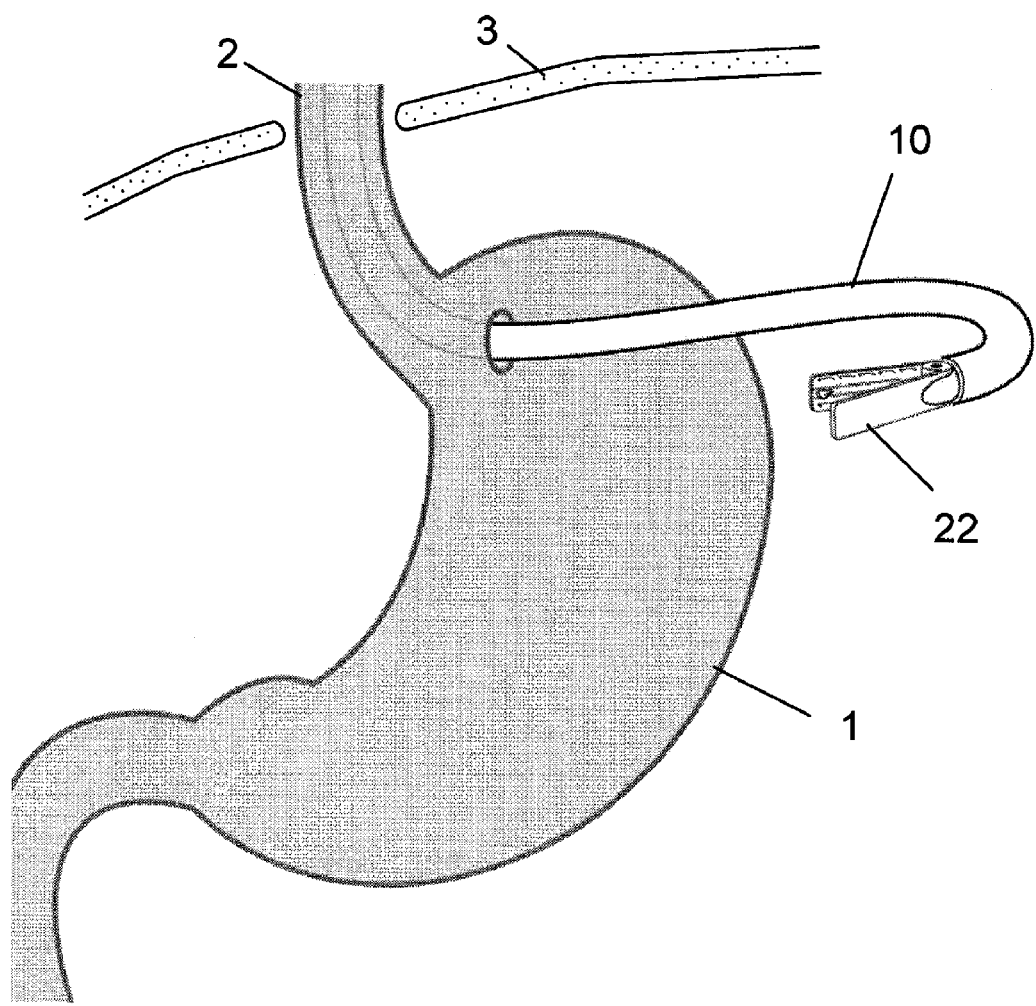
FIGS. 7A to 7C schematically illustrate the steps in dividing the stomach of a patient suffering from sliding hiatal hernia by use of an external endoscopic stapler.
Figure 7B:
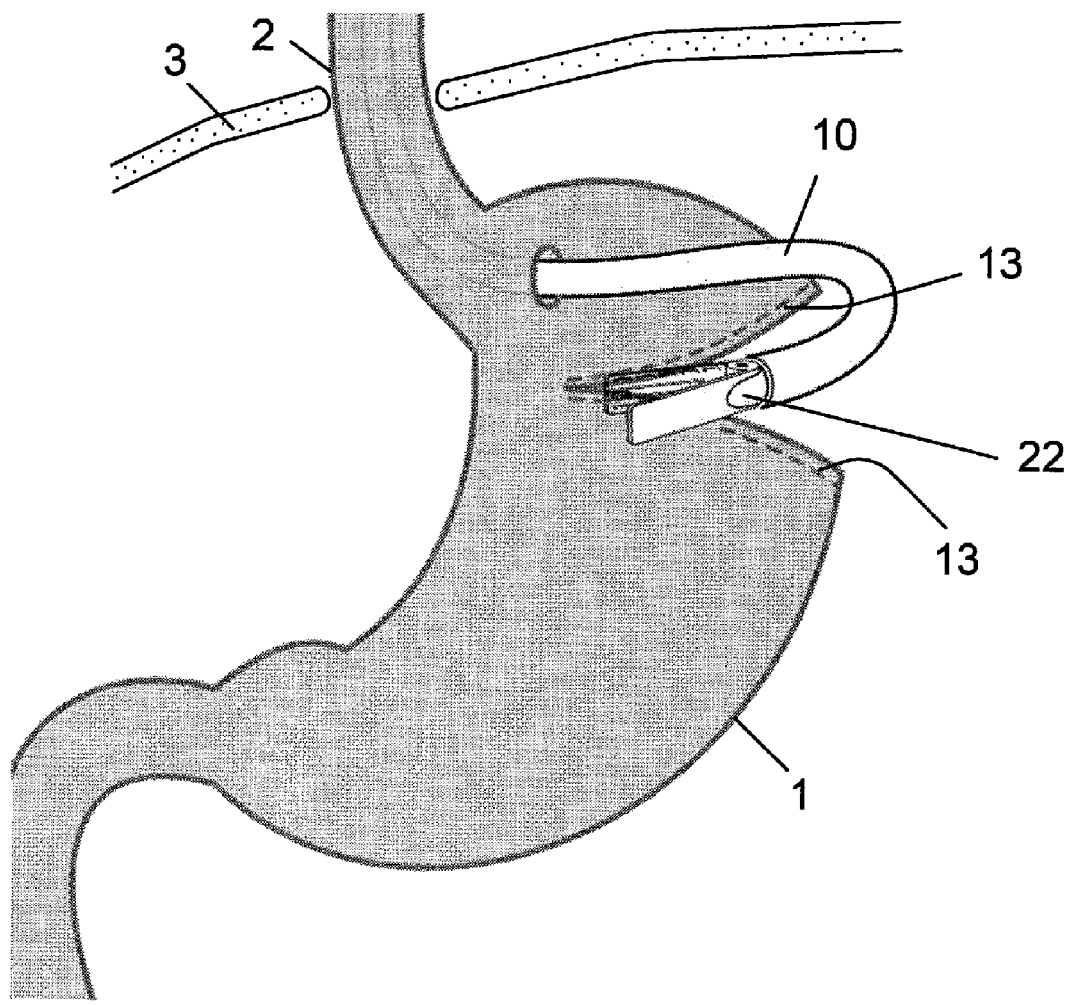
Figure 7C:
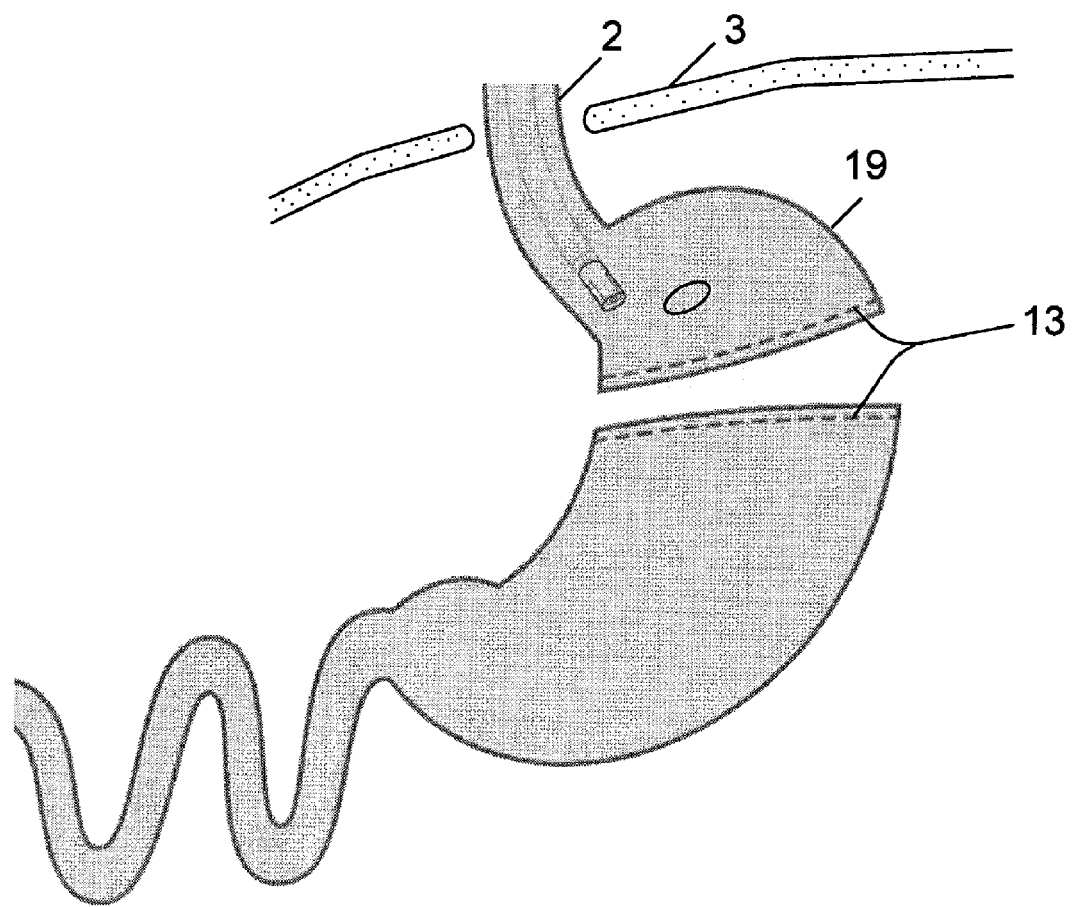

FIGS. 7A to 7C schematically illustrate the steps in dividing the stomach of a patient suffering from sliding hiatal hernia by use of an external endoscopic stapler according to the method of the invention. When laid on the operating table the GEJ of the patient slides above his diaphragm as shown in FIG. 1A. PEEP is then applied as shown in FIG. 2, With the PEEP applied continuously during the entire procedure, the GEJ of the patient is below the diaphragm as shown in FIG. 1B allowing the method of FIGS. 7A to 7C can be carried out.

An endoscope 10 comprising at least one working channel and a linear stapler 22 that applies two parallel lines of staples and a video camera on its distal face is inserted into the stomach 1 through esophagus 2. A cutting tool introduced through the working channel is used to cut a hole in the wall of the upper part of stomach 1. The endoscope is then pushed transgastrically and articulated so that the jaws of the stapler face the exterior of the stomach (FIG. 7A). The jaws of the stapler are then closed grabbing the tissue and an array of staples are fired to make a double line of staples 13 below the hole in the stomach wall. A surgical knife (not shown) in the stapler is activated to cut the tissue between the lines of staples. The jaws of the stapler are then opened, the endoscope is moved forward until more of the stomach is between the walls, the jaws are closed, a second array is fired to lengthen staple lines 1 and the tissue is again cut (FIG. 70B). This procedure is repeated as many times as necessary until the stomach has been bisected into two parts, an upper small pouch 19 and a lower part 1' (FIG. 7C).

Figure 7D:
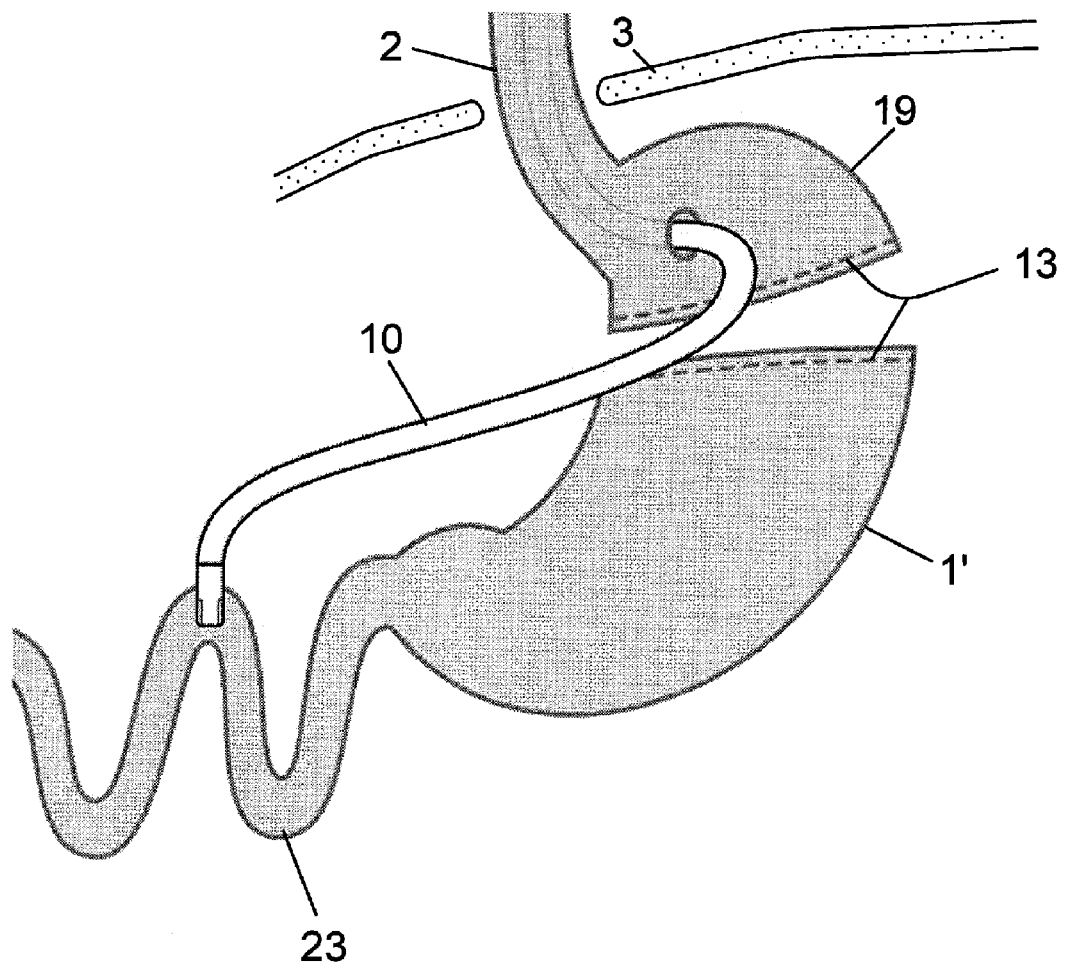
FIGS. 7D and 7E schematically show how the patient's small intestine can be joined to the stomach.
Figure 7E:
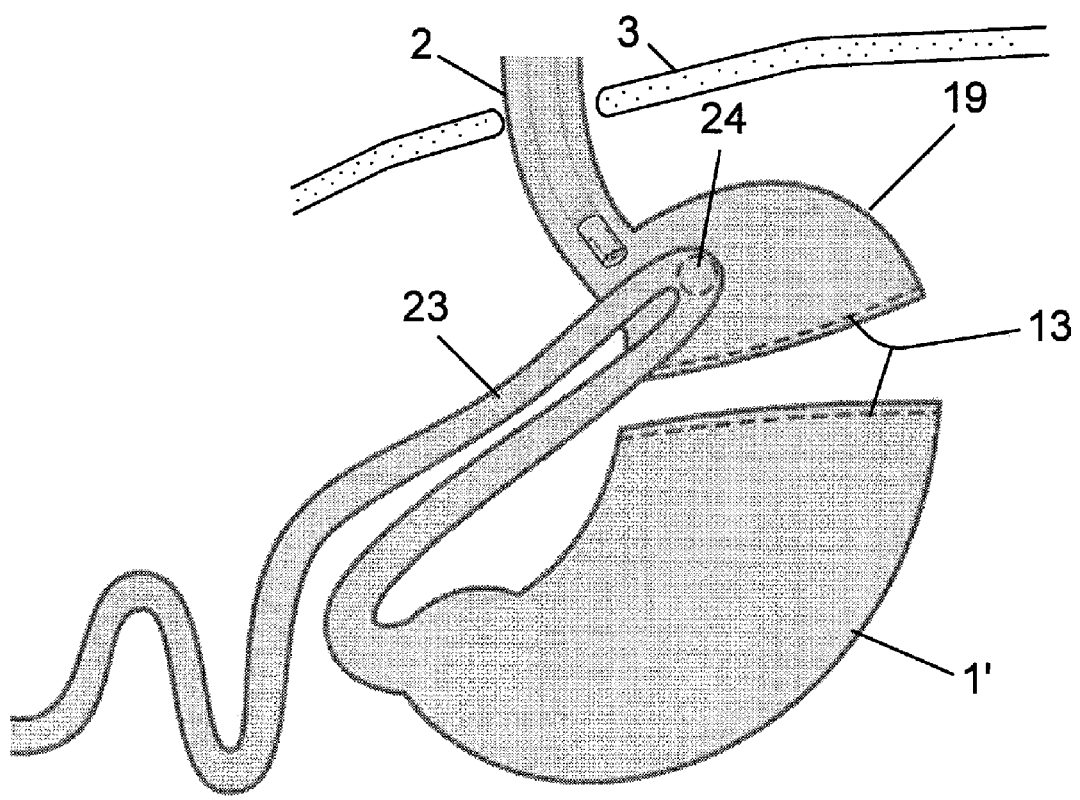

FIGS. 7D and 7E schematically show how the patient's small intestine can be joined to the stomach. Following the procedure described with reference to FIGS. 7A to 7C the endoscope 10 is now maneuvered until it is in a position that a grasping tool can be used to grab the small intestine 23 (FIG. 7D). In order to create a mini gastric bypass, the endoscope is now pulled in the proximal direction until the grabbed part of the intestine is pulled into the hole in pouch 19. A hole is now made in the wall of intestine 23 and it is connected to pouch 19 by conventional means, e.g. an anastomosis button 24, staples, or clips (FIG. 7E).

FIGS. 8A to 8E schematically illustrate the steps in another method for dividing the stomach of a patient suffering from sliding hiatal hernia by use of an external endoscopic stapler according to the method of the invention. When laid on the operating table the GEJ of the patient slides above his diaphragm as shown in FIG. 1A. PEEP is then applied as shown in FIG. 2, With the PEEP applied continuously during the entire procedure, the GEJ of the patient is below the diaphragm as shown in FIG. 1B allowing the method of FIGS. 8A to 8E can be carried out.

Figure 8A:
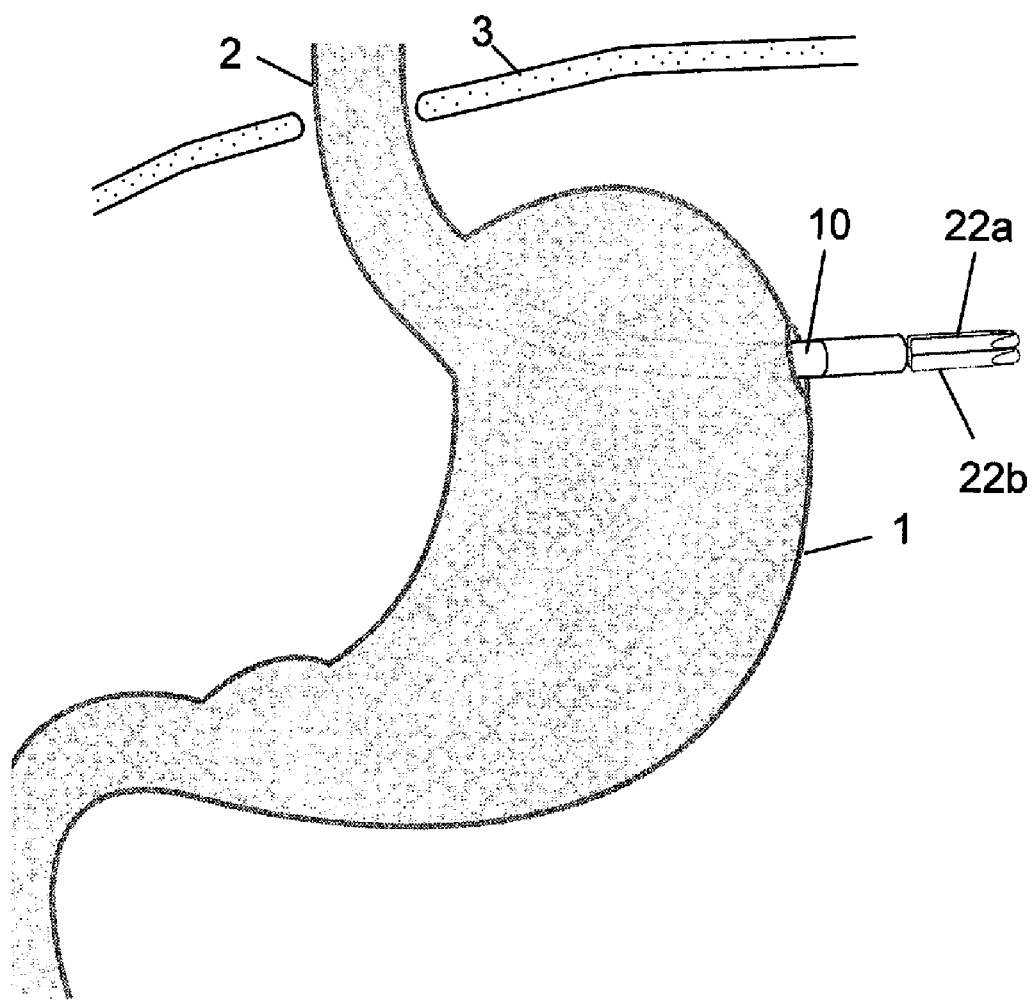
FIGS. 8A to 8E schematically illustrate the steps in another method for dividing the stomach of a patient suffering from sliding hiatal hernia by use of an external endoscopic stapler.
Figure 8B:
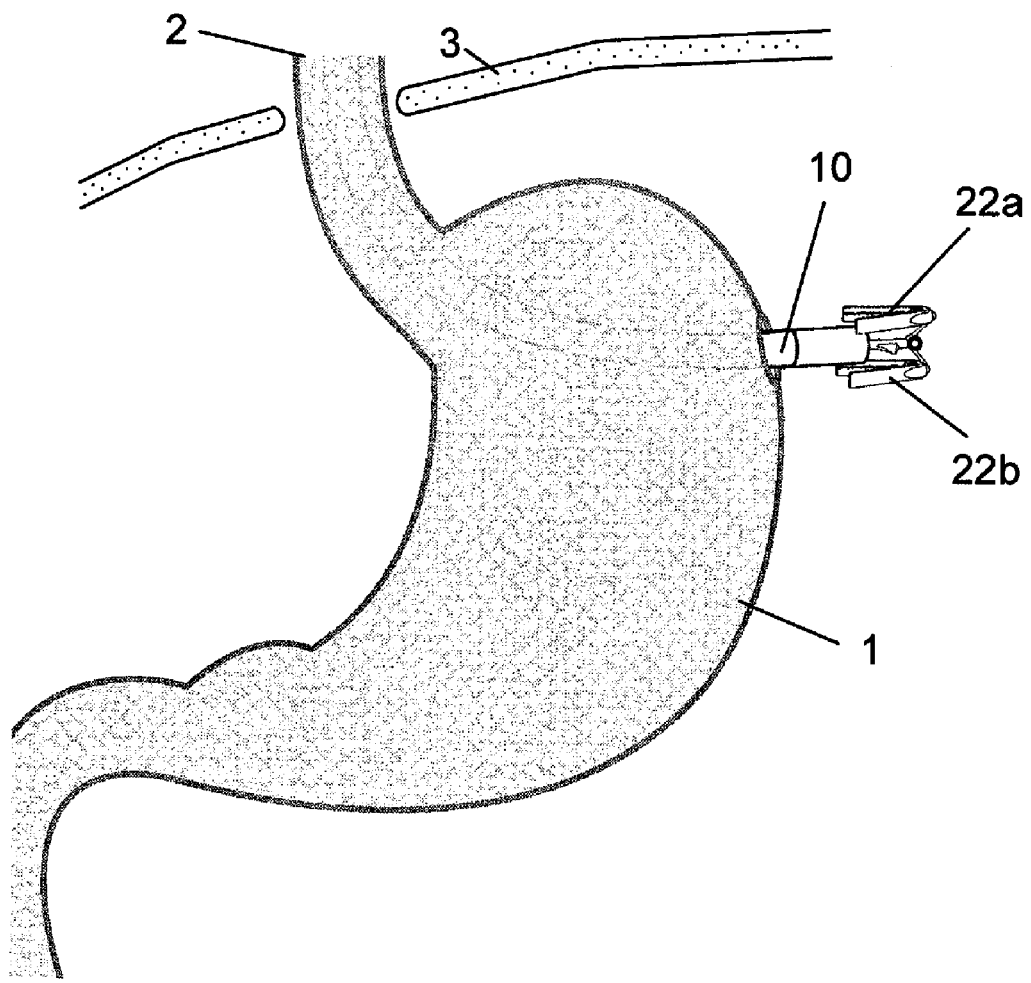
Figure 8C:
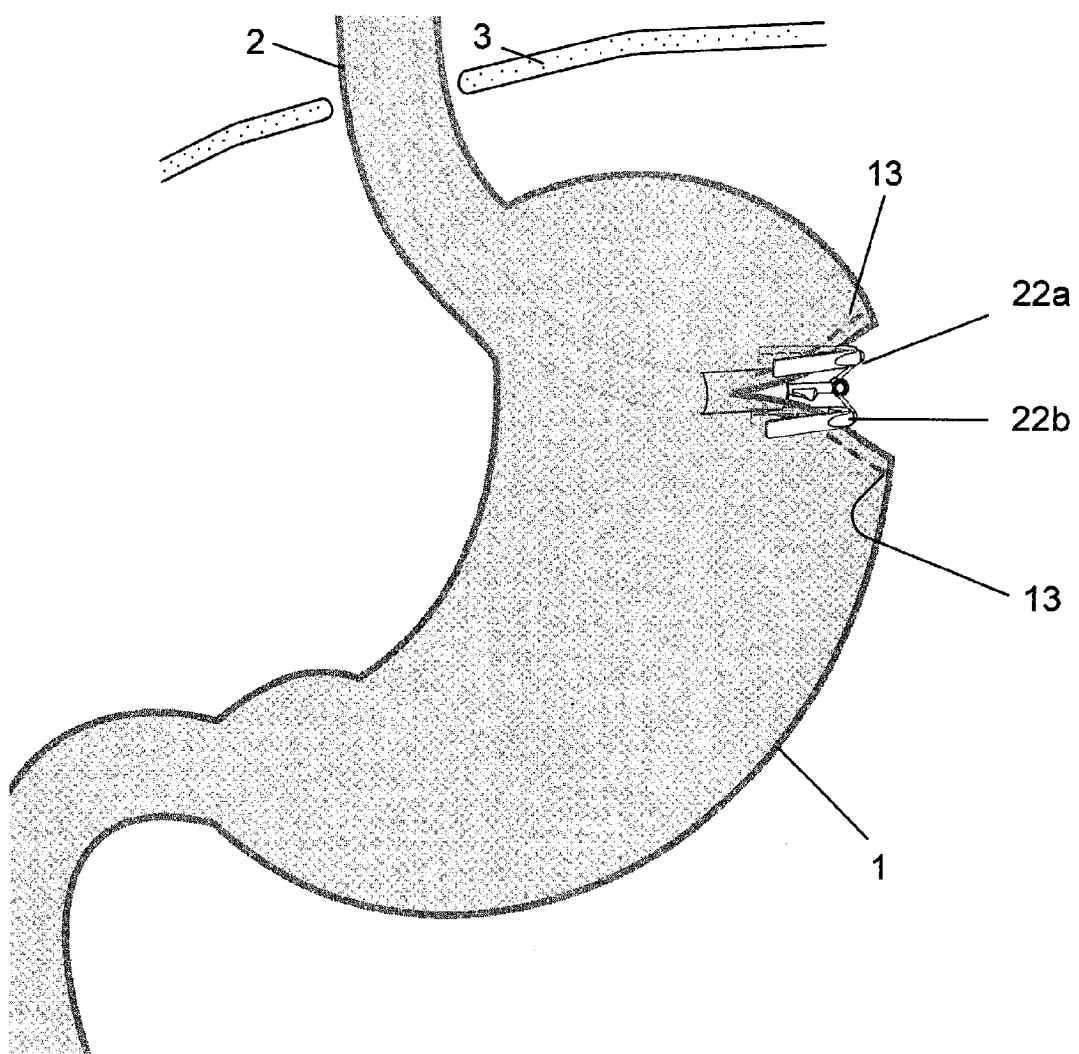
Figure 8D:
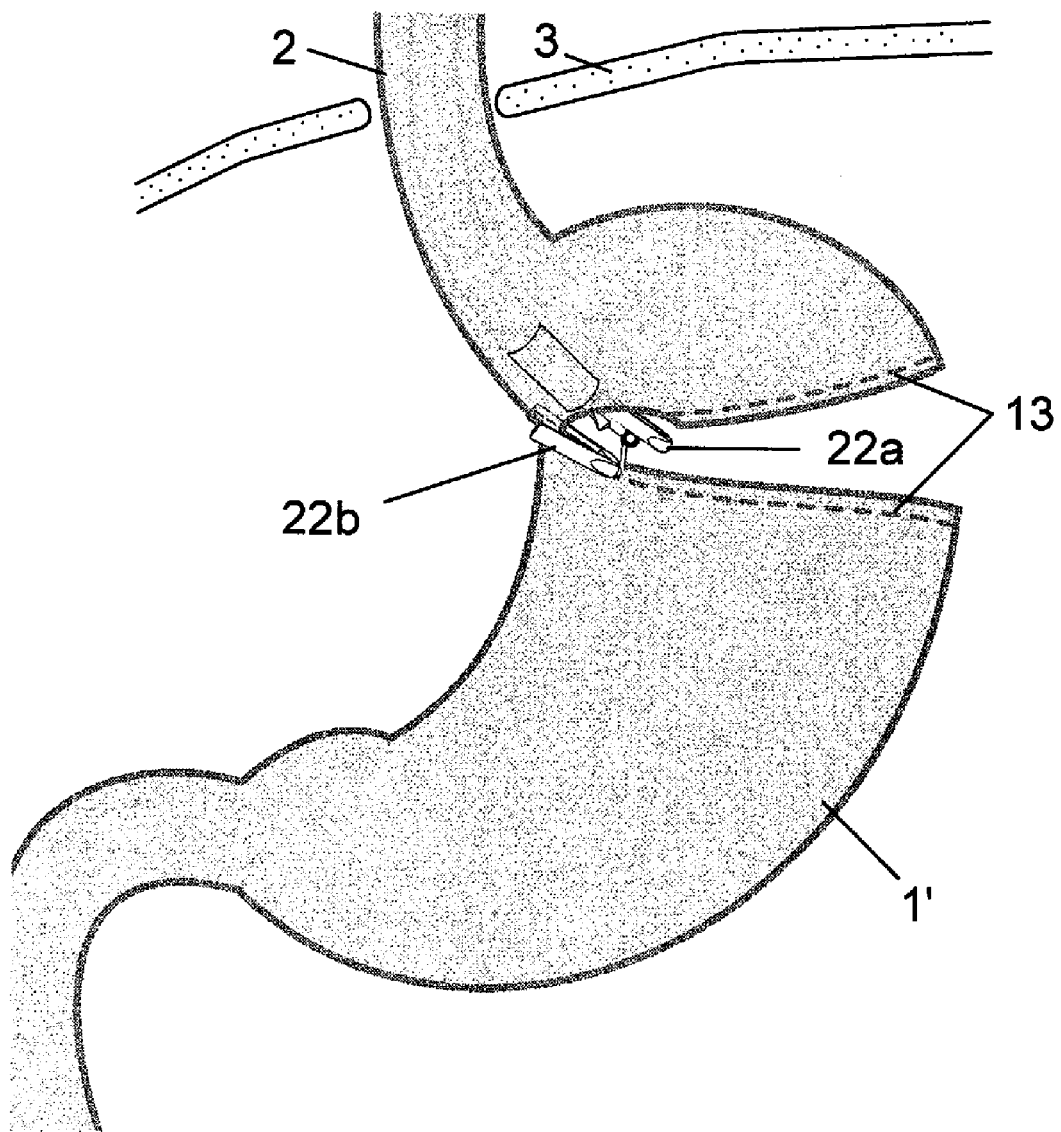
Figure 8E:
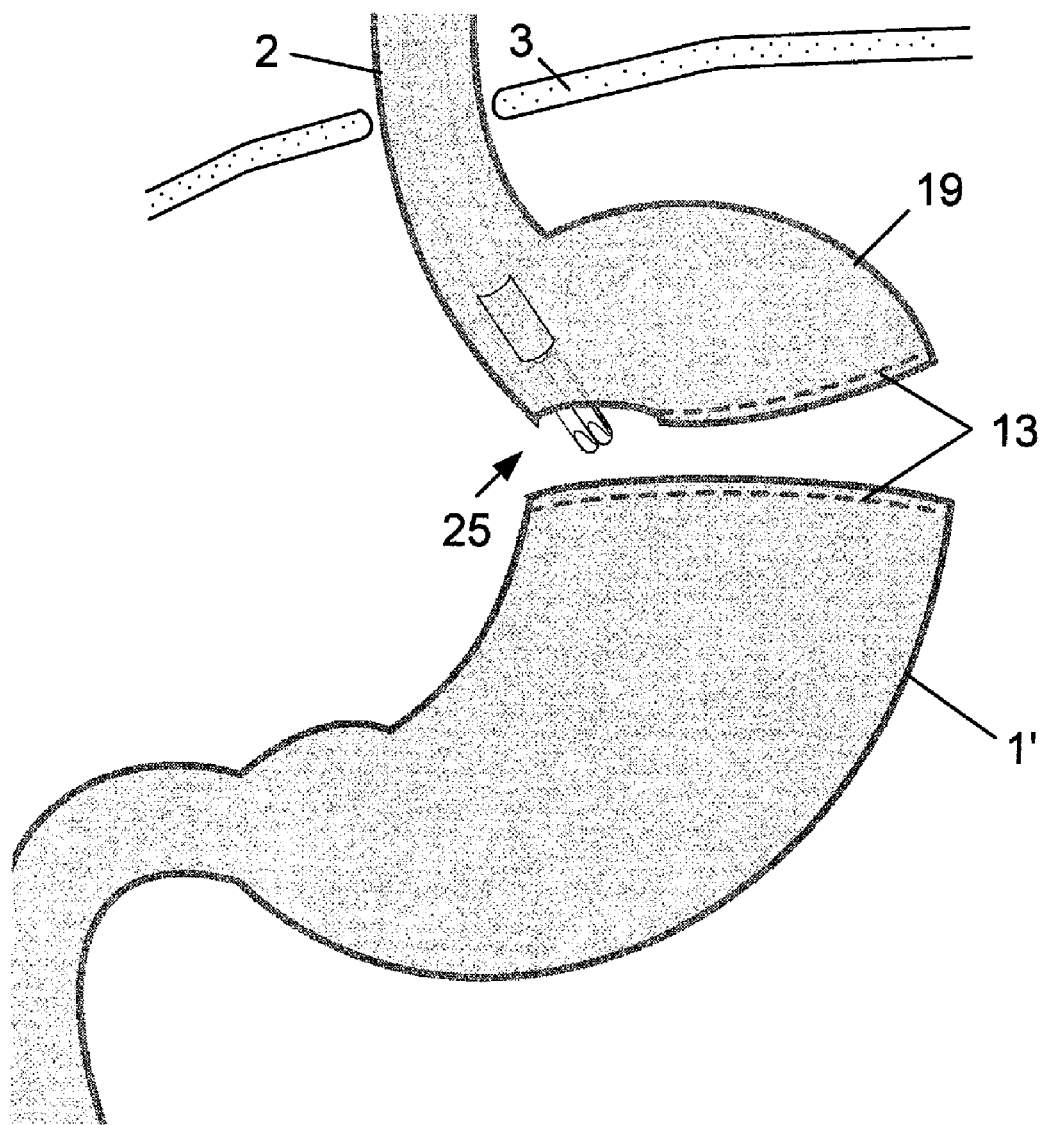

The endoscope is introduced through esophagus 2 into stomach 1. A hole is made in the stomach wall with a surgical cutting tool introduced through a working channel. After the hole has been made, the distal end of endoscope 10, which has two linear staplers 22a and 22b attached to it, is pushed through the hole to the outside of the stomach (FIG. 8A). The jaws of the staplers, which were held in the closed configuration while the endoscope was moved to the operating site, are then spread apart (FIG. 8B). The endoscope is then pulled in the proximal direction, the tissue of the stomach on either side of the hole slides between the open jaws of the staplers, the jaws are closed, and the staples are fired. Each of the staplers 22a and 22b fires an array that produces a single staple line 13. It should be noted that embodiments of linear staplers that apply a double or triple staple line may also be utilized if the surgeon prefers such an approach, as some surgeons currently do in some laparoscopic or open gastric bypass cases. Finally a knife attached to one of the staples is used to slice the tissue between the staple lines (FIG. 8C). The jaws of the staplers are then opened, the endoscope moved proximally and another "bite" is taken increasing the length of staple lines 13. When it is time to perform the last "bite", which will bisect the stomach, stapler 22a is not activated (FIG. 8D). The result is that the stomach is bisected into two parts, the larger lower part 1', whose upper edges are entire closed by staple line 13 and an upper pouch 19, which has a hole 25 in it (FIG. 8E).

Figure 8F:
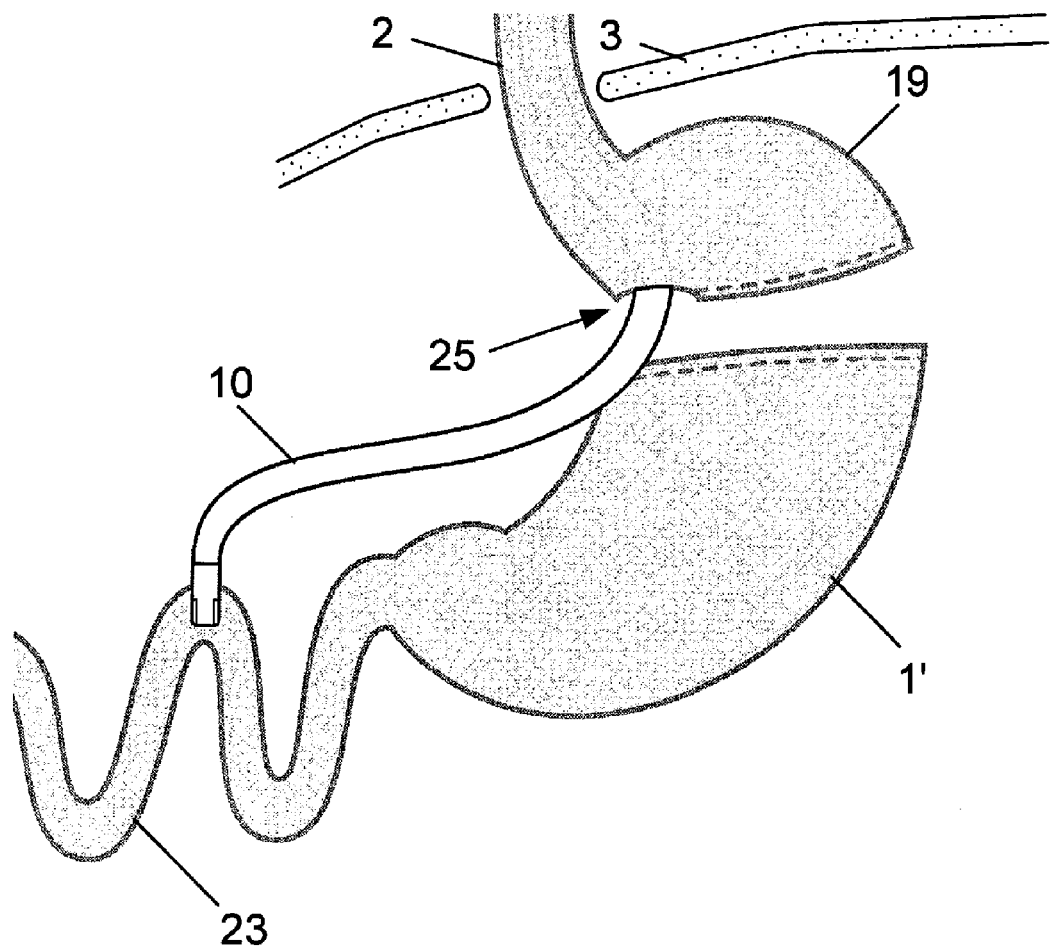
FIGS. 8F and 8G schematically show how the patient's small intestine can be joined to the stomach using the method of FIGS. 8A to 8E.
Figure 8G:
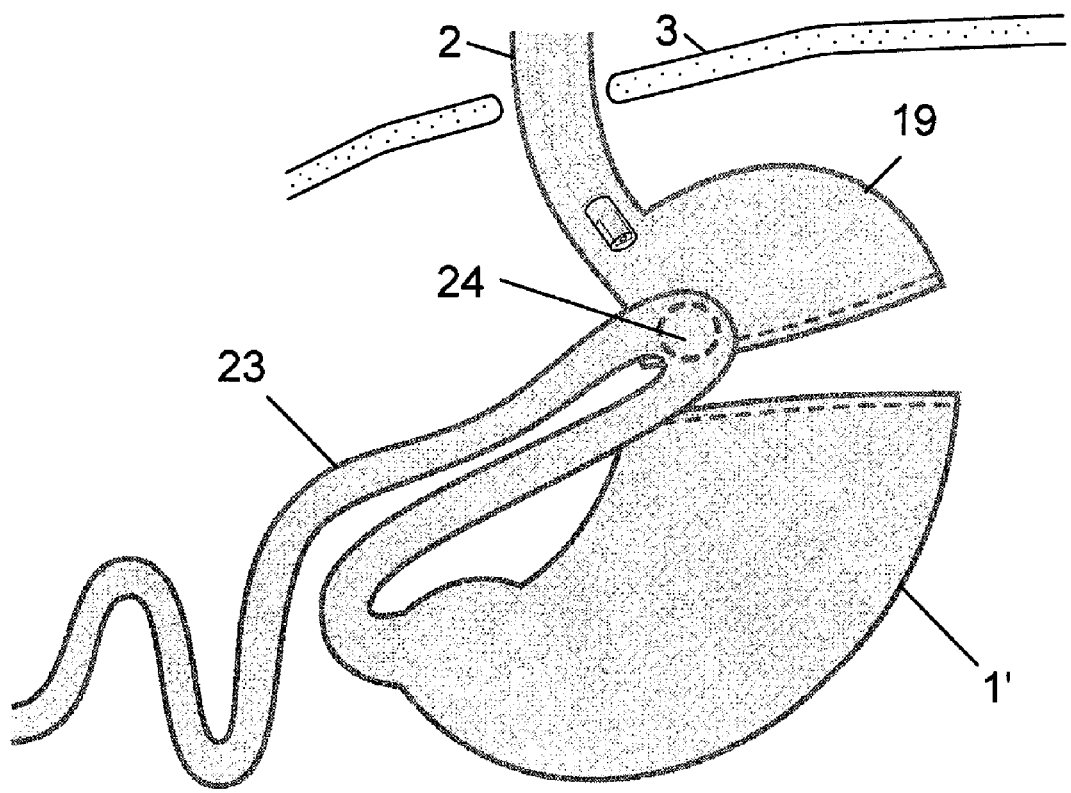

FIGS. 8F and 8G schematically show how the patient's small intestine can be joined to the stomach. After completing the procedure of bisection of the stomach described with reference to FIGS. 8A to 8E, the endoscope with staplers 22a and 22b on the distal end is withdrawn and another endoscope with at least one working channel introduced. The working channel endoscope 10 is pushed through hole 25 in pouch 19 and maneuvered until the intestine 23 can be grabbed (8F). Finally endoscope 10 and grabbed intestine are pulled back to the hole where the intestine 23 is attached to pouch 19 by conventional means, e.g. anastomosis button 25 to complete a mini gastric bypass procedure (FIG. 8G). Starting from the stage shown in FIG. 8E, the surgeon can choose any minimally invasive approach that he wishes to cut the small intestine and connect a Roux limb in order to complete a Roux-en-Y procedure for treatment of morbid obesity.

Figure 9A:
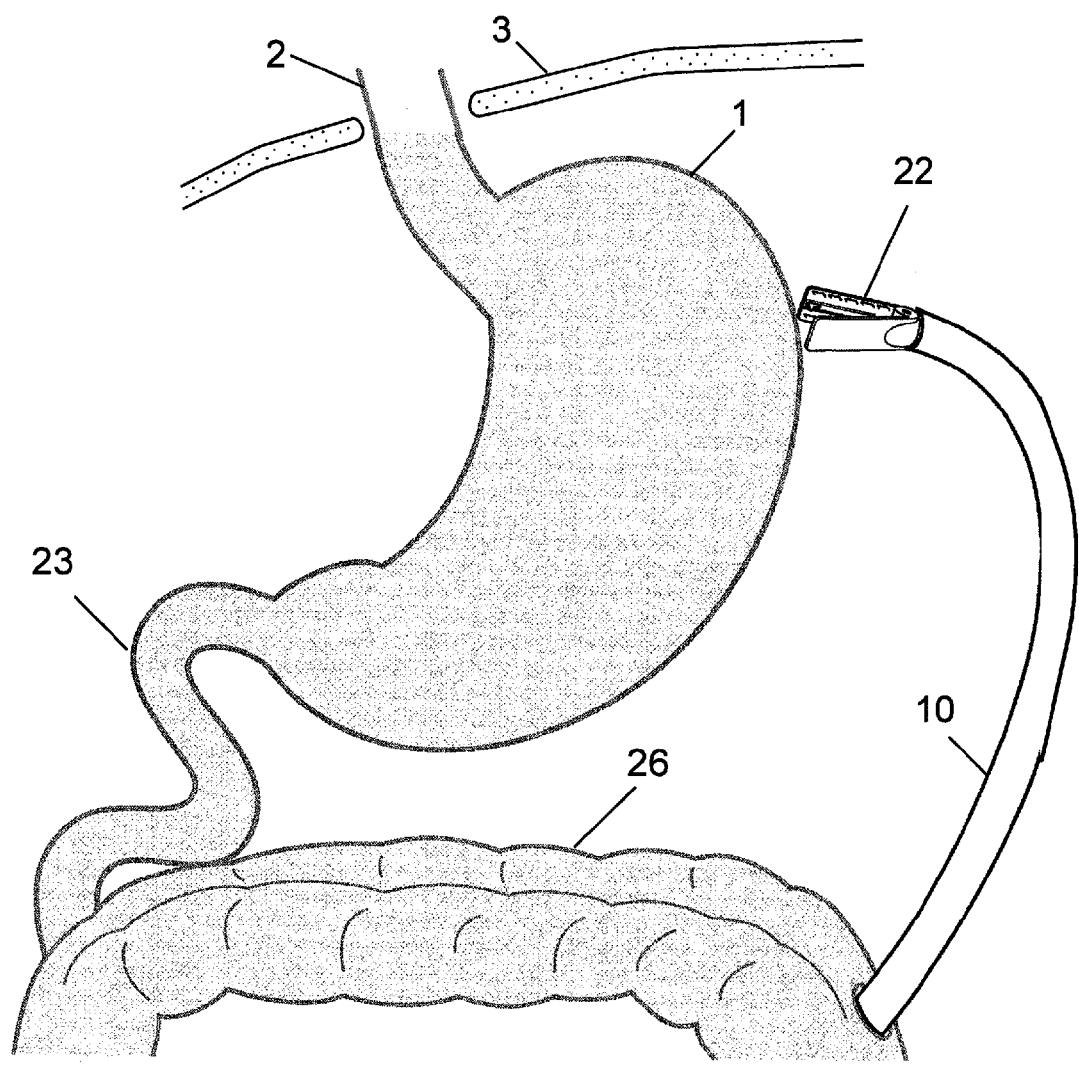
FIGS. 9A to 9C illustrate a second way of endoscopically performing the procedure shown in FIGS. 7A to 7E.
Figure 9B:
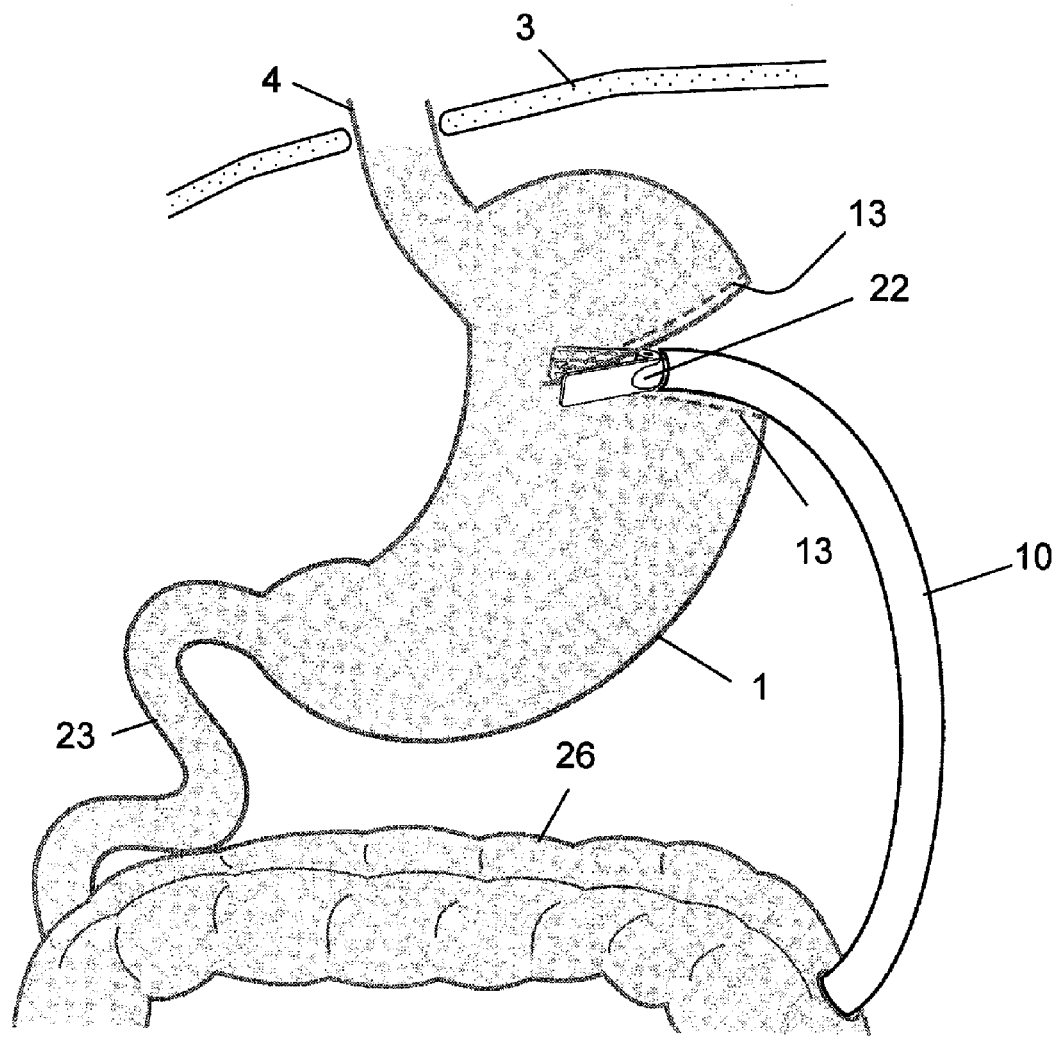
Figure 9C:
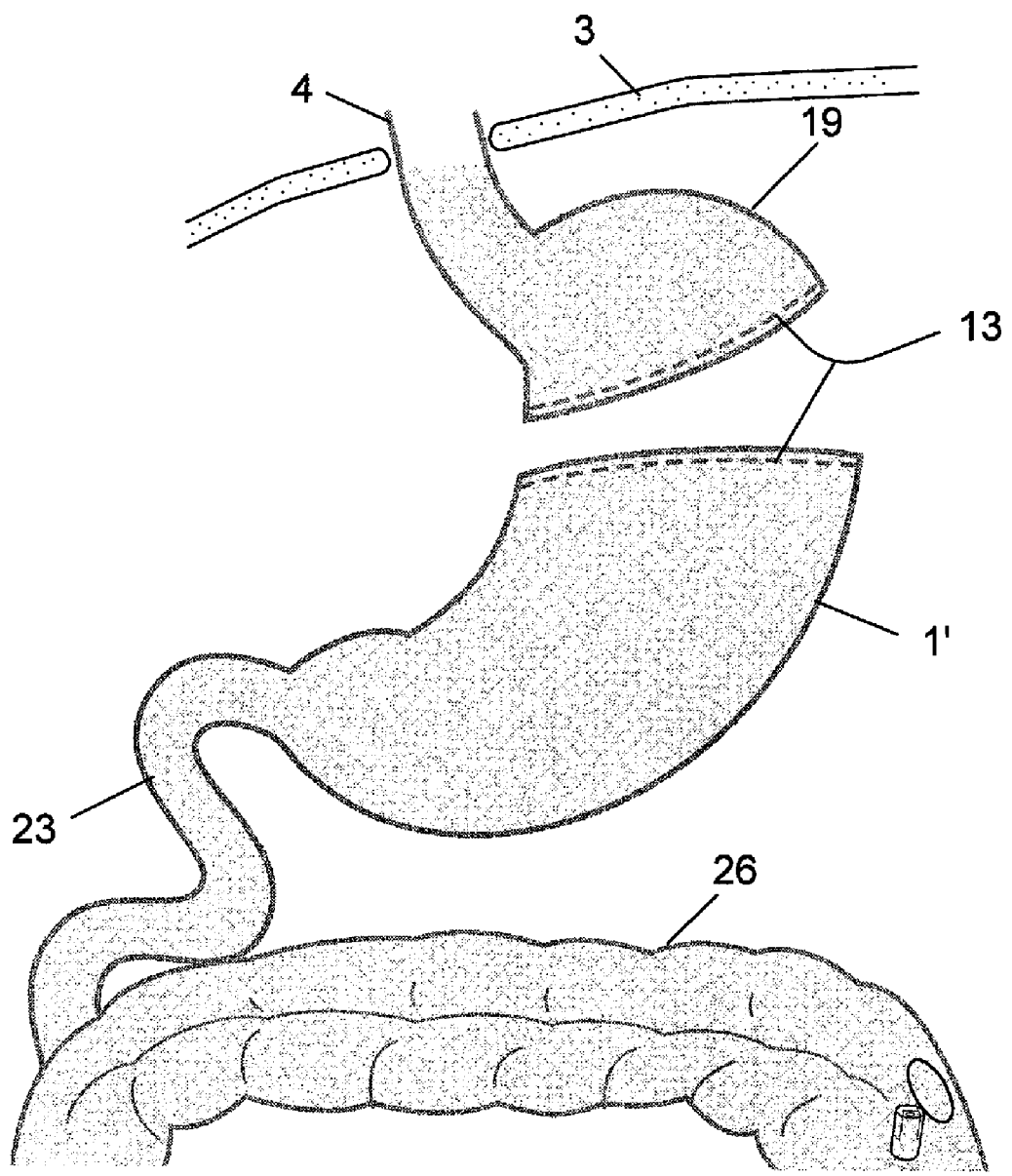

FIGS. 9A to 9C illustrate a second way of endoscopically performing the procedure shown in FIGS. 7A to 7E. After applying the PEEP, instead of starting the procedure by introducing the endoscope transorally, an endoscope 10 is introduced through the anus into the colon. A hole is made in the wall of colon 26 and an endoscopic device 10 comprising linear stapler 22 is pushed out through the hole and advanced until it is facing the stomach 1 (FIG. 9A). The stomach is bisected as described with respect to FIG. 7B. After the stomach is completely bisected to separate pouch 19 from the remainder of the stomach 1', the endoscope with the linear stapler is withdrawn (FIG. 9C). The procedure is completed by introducing a working channel endoscope through the hole in the colon to bring a loop of intestine 23 (transected as a Roux limb or not transected as in a mini gastric bypass) to the pouch 19. In this trans colon approach the operating tools are already in the abdominal cavity, therefore the entire procedure can be completed without entering the esophagus 4 and making a hole in the stomach 1. After connecting the loop to the bowel an endoscope with stapler on the distal end is introduced to the colon and used to seal the hole.

FIGS. 10A to 10D schematically illustrate the steps in performing a transgastric fundoplication procedure on a patient suffering from sliding hiatal hernia. When laid on the operating table the GEJ of the patient slides above his diaphragm as shown in FIG. 1A. PEEP is then applied as shown in FIG. 2, With the PEEP applied continuously during the entire procedure, the GEJ of the patient is below the diaphragm as shown in FIG. 1B allowing the method of FIGS. 10A to 10D to be carried out.

The endoscope 10 is introduced in its straightened configuration through the mouth of the patient and the esophagus 2 into the stomach 1. After the distal end of the endoscope enters the interior of the stomach, the articulation section is slightly bent and the distal face is guided to a location close to the anterior wall near the greater curvature 16. This is the situation shown in FIG. 10A. At this point a hole is cut in the anterior wall by means of a surgical tool, e.g. a RF cutter, that is guided to the site through a working channel in the endoscope 1.

Figure 10A:
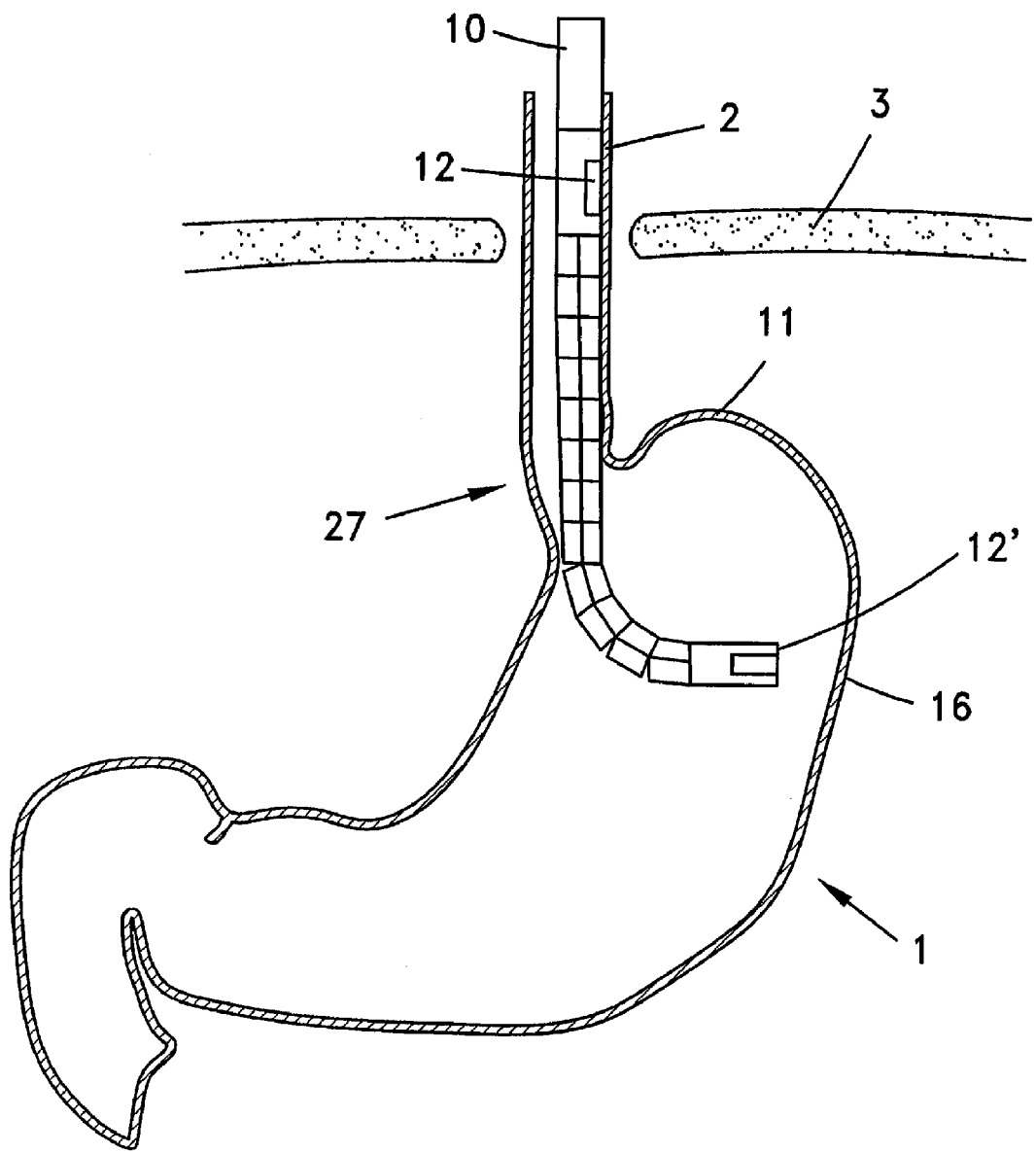
FIGS. 10A to 10D schematically illustrate the steps in a transgastric fundoplication procedure.
Figure 10B:
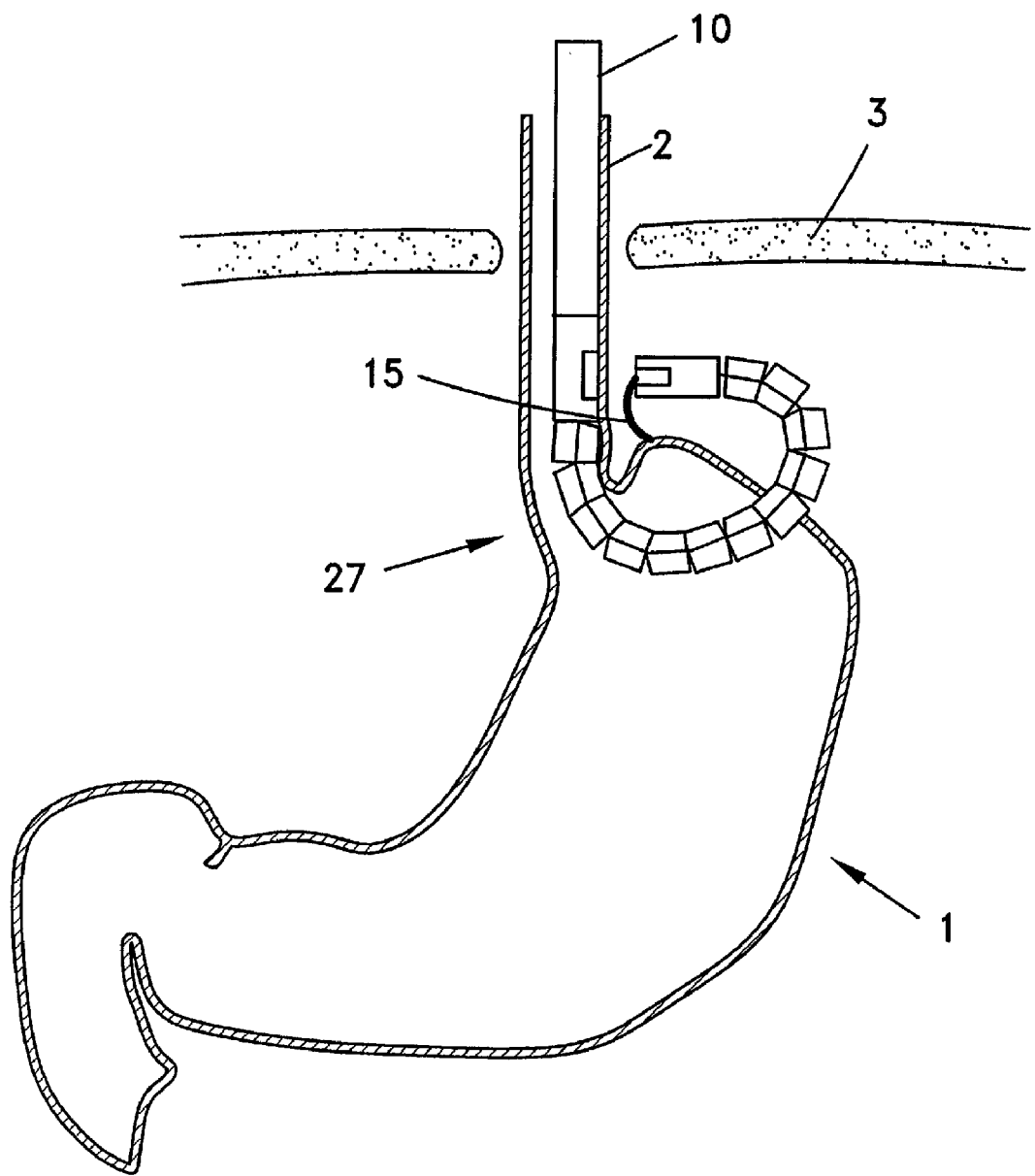

Once the hole is made, the cutting device is withdrawn from the working channel and the distal tip of the endoscope is pushed through the hole to the outside of the stomach. The endoscope is further advanced distally and the articulation section bent until the distal tip is close to the outer wall of the fundus 11. In this location, as shown in FIG. 10B, the tissue on the outer wall of the fundus 11 is grabbed by a gabbing tool, e.g. forceps 15, that exits the distal face of endoscope 1 through a working channel.

Figure 10C:
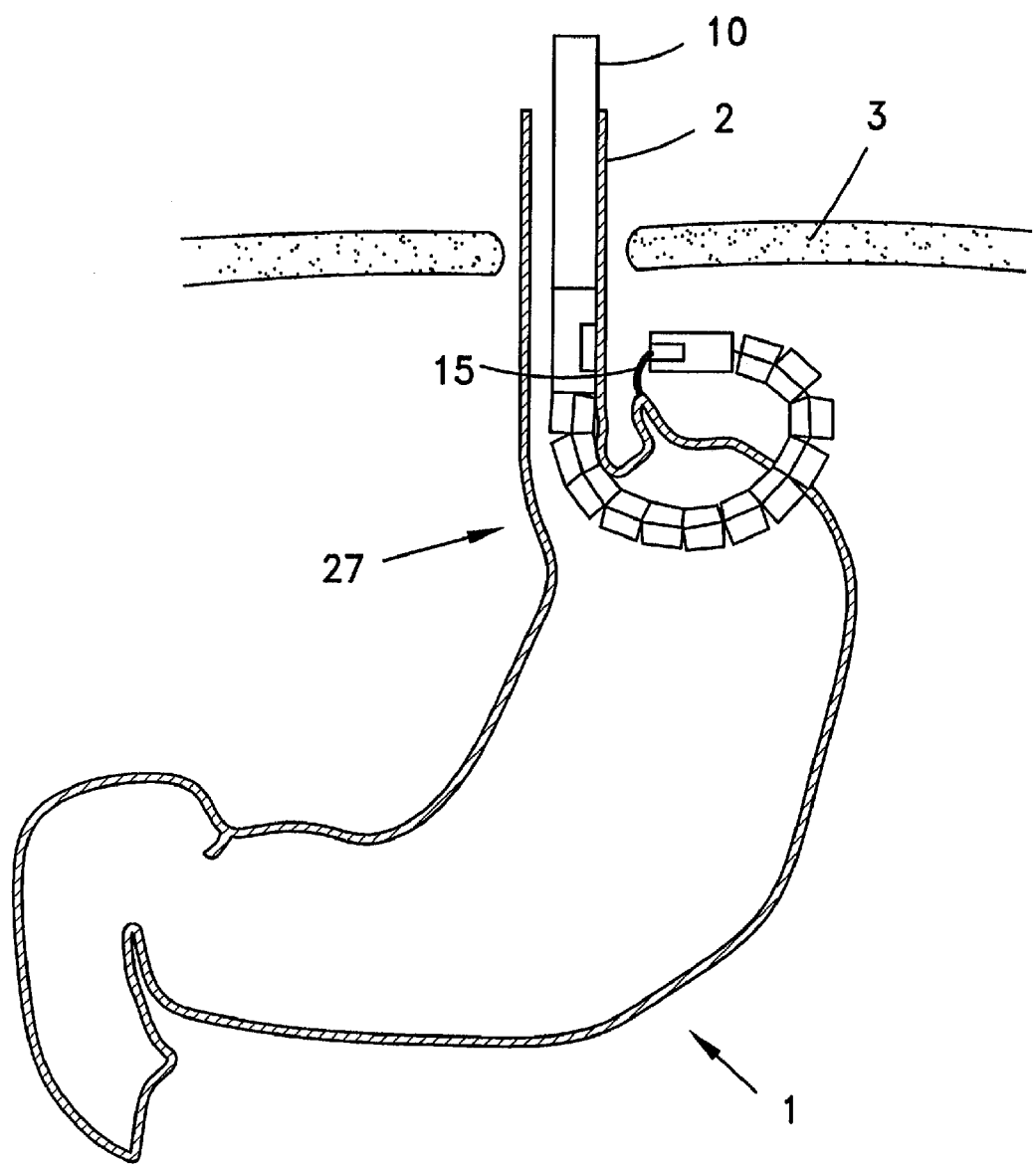

After the tissue has been grabbed, the articulation section is further bent and moved until the grabbed tissue of the fundus is pulled close to the outer wall of the esophagus as shown in FIG. 10C. At this point, the curved endoscope is moved as necessary until the stapler cartridge is located in the esophagus a distance about three centimeters above the entrance to the stomach 27 and rotated until it faces the direction of the greater curvature 16 of the stomach 1.

Figure 10D:
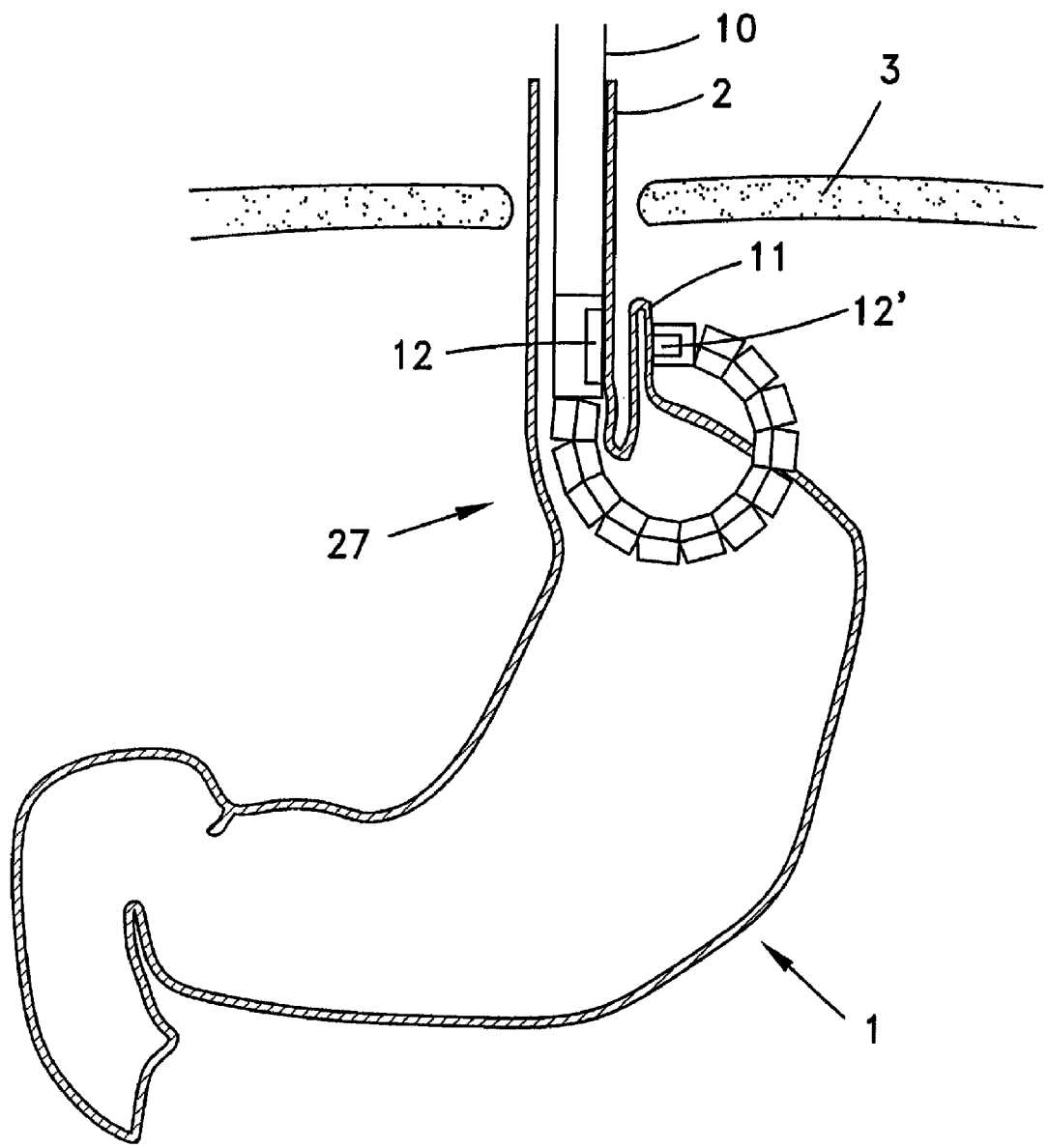

The forceps 15 are now pulled proximally and, as the articulation section continues to be bent, the distal face approaches the outer wall of esophagus 2, pressing the tissue of the fundus 11 between the distal face of endoscope 1, on which is located the face of stapler anvil 12', and the outer wall of esophagus 2. At this point, which is shown in FIG. 10D, the firing cable is pulled and the array of staples is fired from staple cartridge 12 against anvil 12'.

In the preferred embodiment of the partial fundoplication procedure, the endoscope is partially straightened, rotated to a new location and the tissue of the stomach is attached to the esophagus one or two additional times. Finally the endoscope is pulled back into the stomach, the hole in the stomach wall is closed, and all instruments are withdrawn from the body of the patient.

The invention claimed is:

1. A method for treating a hiatal hernia comprising the steps of lowering a patient's gastroesophageal junction below the patient's diaphragm during the performance of surgical procedures performed via at least one natural orifice, said patient having a sliding hiatal hernia, wherein said step of lowering consists essentially of applying positive pressure ventilation with positive end expiratory pressure (PEEP) to said patient.

2. The method according to claim 1, comprising tilting an operating table slightly downwards.

3. The method according to claim 1, wherein the PEEP is in a range of approximately 5-10 mmHg and is applied during the entire surgical procedures.

4. The method according to claim 1, wherein, after the PEEP is applied to lower the gastroesophageal junction below the diaphragm, the patient's stomach is joined to the patient's esophagus by applying fixing means.

5. The method according to claim 4 wherein the surgical procedures include a fundoplication.

6. The method according to claim 1 wherein the surgical procedures include a surgical treatment of morbid obesity.

7. The method according to claim 1 wherein the surgical procedures include a correction of the hiatal hernia.

8. The method according to claim 1 wherein the surgical procedures include a removal of part or parts of the patient's stomach.

9. The method according to claim 1 wherein the surgical procedures comprise inserting or attaching one or more implanted devices to the patient's esophagus or the patient's stomach wall.

10. The method according to claim 1 wherein the surgical procedures comprises inserting or attaching one or more external devices to the patient's stomach wall.

11. The method according to claim 1 wherein the surgical procedures comprises dividing the patient's stomach by use of an external stapler or an endoscopic stapler.

12. The method according to claim 1 wherein the surgical procedures comprises a treatment or removal of part of the patient's intestine.

13. The method according to claim 1, wherein, after the PEEP is applied to lower the gastroesophageal junction below the patient's diaphragm, an incision is made in the patient's stomach and a transgastric procedure is performed comprising joining the stomach to the patient's small intestine by applying fixing means.

14. The method according to claim 1, wherein, after the PEEP is applied to lower the patient's gastroesophageal junction below the patient's diaphragm, an incision is made in the patient's stomach and a transgastric procedure is performed comprising dividing the stomach into two different volumes.

15. The method according to claim 1, wherein, after the PEEP is applied to lower the patient's gastroesophageal junction below the patient's diaphragm, an incision is made in the patient's stomach and a transgastric fundoplication is performed comprising joining the stomach to the patient's esophagus by applying fixing means.

16. The method according to claim 1, wherein, after the PEEP is applied to lower the patient's gastroesophageal junction below the patient's diaphragm, an incision is made in the patient's stomach and the stomach is transgastrically attached/joined to the patient's small intestine by applying fixing means.

17. The method according to claim 1, wherein, after the PEEP is applied to lower the patient's gastroesophageal junction below the patient's diaphragm, an incision is made in the patient's stomach and the patient's intestine is treated or part of it is removed transgastrically.

* * * * *